(12) United States Patent
Matsuno et al.

(10) Patent No.: US 10,107,802 B2
(45) Date of Patent: Oct. 23, 2018

(54) METHOD FOR MEASURING MODIFIED NUCLEOBASE USING SOLID PHASE PROBE, AND KIT FOR SAME

(71) Applicant: FUJIREBIO INC., Shinjuku-ku (JP)

(72) Inventors: Tatsuki Matsuno, Tokyo (JP); Mariko Horiike, Tokyo (JP)

(73) Assignee: FUJIREBIO INC., Shinjuku-ku (JP)

( * ) Notice: Subject to any disclaimer, the term of this patent is extended or adjusted under 35 U.S.C. 154(b) by 98 days.

(21) Appl. No.: 14/913,195

(22) PCT Filed: Aug. 20, 2014

(86) PCT No.: PCT/JP2014/071704
§ 371 (c)(1),
(2) Date: Feb. 19, 2016

(87) PCT Pub. No.: WO2015/025863
PCT Pub. Date: Feb. 26, 2015

(65) Prior Publication Data
US 2016/0274096 A1 Sep. 22, 2016

(30) Foreign Application Priority Data

Aug. 21, 2013 (JP) .................................. 2013-171659

(51) Int. Cl.
*G01N 33/68* (2006.01)
*G01N 33/543* (2006.01)
(Continued)

(52) U.S. Cl.
CPC ..... *G01N 33/54306* (2013.01); *C12Q 1/6804* (2013.01); *C12Q 1/6834* (2013.01);
(Continued)

(58) Field of Classification Search
None
See application file for complete search history.

(56) References Cited

U.S. PATENT DOCUMENTS 6,361,947 B1 * 3/2002 Dong .................. C12Q 1/6837
435/6.12
6,989,235 B2 * 1/2006 Chapsky ................. B82Y 5/00
435/6.16
(Continued)

FOREIGN PATENT DOCUMENTS

EP          2 281 883 A1      2/2011
JP          2012-230019       11/2012
(Continued)

OTHER PUBLICATIONS

Extended European Search Report dated Mar. 31, 2017 in Patent Application No. 14837574.4.
(Continued)

*Primary Examiner* — Changhwa J Cheu
(74) *Attorney, Agent, or Firm* — Oblon, McClelland, Maier & Neustadt, L.L.P.

(57) ABSTRACT

The present invention provides a technique that suppresses a background value of a detection signal to construct an immunoassay system that detects a modified nucleobase. Specifically, the present invention provides a method for measuring a modified nucleobase including incubating a nucleic acid sample, a capture probe, and a solid phase probe in a solution and measuring a modified nucleobase using an antibody against the modified nucleobase in the obtained solution. The present invention also provides a kit for measuring a modified nucleobase including a capture probe, a solid phase probe, and an antibody against a modified nucleobase.

8 Claims, 11 Drawing Sheets

Specification includes a Sequence Listing.

(51) Int. Cl.
  *C12Q 1/6804* (2018.01)
  *C12Q 1/6834* (2018.01)
  *G01N 33/53* (2006.01)

(52) U.S. Cl.
  CPC ... *G01N 33/5308* (2013.01); *G01N 33/54393* (2013.01); *G01N 33/68* (2013.01)

(56) References Cited

U.S. PATENT DOCUMENTS

| 2008/0124735 | A1* | 5/2008 | Schuster | C12Q 1/6818 435/6.12 |
|---|---|---|---|---|
| 2009/0068649 | A1 | 3/2009 | Maki et al. | |
| 2012/0107808 | A1 | 5/2012 | Li et al. | |

FOREIGN PATENT DOCUMENTS

| WO | WO 90/10717 A1 | 9/1990 |
|---|---|---|
| WO | WO 2004/020654 A2 | 3/2004 |
| WO | WO 2004/020654 A3 | 3/2004 |

OTHER PUBLICATIONS

Ekaterina Olkhov-Mitsel, et al., "Strategies for discovery and validation of methylated and hydroxymethylated DNA biomarkers" Cancer Medicine, XP055145378, vol. 1, No. 2, Oct. 14, 2012, pp. 237-260.

Johannes Proll, et al., "Ultra-Sensitive Immunodetection of 5'Methyl Cytosine for DNA Methylation Analysis on Oligonucleotide Microarrays" DNA Research , vol. 13, 2006, pp. 37-42.

Ryoji Kurita, et al. "DNA Methylation Analysis Triggered by Bulge Specific Immuno-Recognition" Analytical Chemistry, vol. 84, No. 17, 2012, pp. 7533-7538.

Ryoji Kurita "DNA Methylation Analysis by Electrogenerated Chemiluminescence and Bulge-Specific Immuno-Recognition" Journal of the Society for Chemistry and Micro-Nano Systems, vol. 12, No. 1, Mar. 2013, 10 pages.

International Search Report dated Nov. 25, 2014 for PCT/JP2014/071704 filed on Aug. 20, 2014.

* cited by examiner

SEQUENCE LISTING

<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: Solid phase probe

<400> SEQUENCE: 1
tttttttttt tttttttttt                        20

<210> SEQ ID NO 2

```
<211> LENGTH: 40
<212> TYPE: DNA
<213> ORGANISM: Artificial Sequence
<220> FEATURE:
<223> OTHER INFORMATION: Solid phase probe

<400> SEQUENCE: 2
tttttttttt tttttttttt tttttttttt tttttttttt                              40

<210> SEQ ID NO 3
<211> LENGTH: 20
<212> TYPE: DNA
<213> ORGANISM: Artificial Sequence
<220> FEATURE:
<223> OTHER INFORMATION: Solid phase probe

<400> SEQUENCE: 3
aaaaaaaaaa aaaaaaaaaa                                                    20

<210> SEQ ID NO 4
<211> LENGTH: 20
<212> TYPE: DNA
<213> ORGANISM: Artificial Sequence
<220> FEATURE:
<223> OTHER INFORMATION: Solid phase probe

<400> SEQUENCE: 4
gggggggggg gggggggggg                                                    20

<210> SEQ ID NO 5
<211> LENGTH: 20
<212> TYPE: DNA
<213> ORGANISM: Artificial Sequence
<220> FEATURE:
<223> OTHER INFORMATION: Solid phase probe

<400> SEQUENCE: 5
cccccccccc cccccccccc                                                    20

<210> SEQ ID NO 6
<211> LENGTH: 40
<212> TYPE: DNA
<213> ORGANISM: Artificial Sequence
<220> FEATURE:
<223> OTHER INFORMATION: Solid phase probe

<400> SEQUENCE: 6
cccccccccc cccccccccc cccccccccc cccccccccc                              40

<210> SEQ ID NO 7
<211> LENGTH: 40
<212> TYPE: DNA
<213> ORGANISM: Artificial Sequence
<220> FEATURE:
<223> OTHER INFORMATION: Solid phase probe

<400> SEQUENCE: 7
cccccctaga aaattgagaga agtccaccac aaaaaaaaaa                             40

<210> SEQ ID NO 8
<211> LENGTH: 41
<212> TYPE: DNA
<213> ORGANISM: Artificial Sequence
<220> FEATURE:
<223> OTHER INFORMATION: Solid phase probe

<400> SEQUENCE: 8
```

-continued cactgaacaa atggcactag taaactgagc caaaaaaaaa a       41

<210> SEQ ID NO 9
<211> LENGTH: 26
<212> TYPE: DNA
<213> ORGANISM: Artificial Sequence
<220> FEATURE:
<223> OTHER INFORMATION: Solid phase probe

<400> SEQUENCE: 9
gaagtcaaca ggacgacgcc gcgcaa       26

<210> SEQ ID NO 10
<211> LENGTH: 27
<212> TYPE: DNA
<213> ORGANISM: Artificial Sequence
<220> FEATURE:
<223> OTHER INFORMATION: Solid phase probe

<400> SEQUENCE: 10
gaagtcaaca ggacggacgc cgcgcaa       27

<210> SEQ ID NO 11
<211> LENGTH: 27
<212> TYPE: DNA
<213> ORGANISM: Artificial Sequence
<220> FEATURE:
<223> OTHER INFORMATION: Nucleotide sequence of a certain target nucleic
      acid. The 13th nucleotide (cytosine) is methylated at position 5.

<400> SEQUENCE: 11
ttgcgcggcg tccgtcctgt tgacttc       27

<210> SEQ ID NO 12
<211> LENGTH: 46
<212> TYPE: DNA
<213> ORGANISM: Artificial Sequence
<220> FEATURE:
<223> OTHER INFORMATION: Capturing probe

<400> SEQUENCE: 12
gaagtcaaca ggacgacgcc gcgcaaaaaa aaaaaaaaaa aaaaaa       46

<210> SEQ ID NO 13
<211> LENGTH: 40
<212> TYPE: DNA
<213> ORGANISM: Artificial Sequence
<220> FEATURE:
<223> OTHER INFORMATION: Solid phase probe

<400> SEQUENCE: 13
tttttttttt tttttttttt tttttttttt tttttttttt       40

<210> SEQ ID NO 14
<211> LENGTH: 46
<212> TYPE: DNA
<213> ORGANISM: Artificial Sequence
<220> FEATURE:
<223> OTHER INFORMATION: Capturing probe

<400> SEQUENCE: 14
gaagtcaaca ggacgacgcc gcgcaattttt tttttttttt tttttt       46

<210> SEQ ID NO 15
<211> LENGTH: 20

```
<212> TYPE: DNA
<213> ORGANISM: Artificial Sequence
<220> FEATURE:
<223> OTHER INFORMATION: Solid phase probe

<400> SEQUENCE: 15
aaaaaaaaaa aaaaaaaaaa                                              20

<210> SEQ ID NO 16
<211> LENGTH: 46
<212> TYPE: DNA
<213> ORGANISM: Artificial Sequence
<220> FEATURE:
<223> OTHER INFORMATION: Capturing probe

<400> SEQUENCE: 16
gaagtcaaca ggacgacgcc gcgcaacccc cccccccccc ccccc                  46

<210> SEQ ID NO 17
<211> LENGTH: 20
<212> TYPE: DNA
<213> ORGANISM: Artificial Sequence
<220> FEATURE:
<223> OTHER INFORMATION: Solid phase probe

<400> SEQUENCE: 17
gggggggggg gggggggggg                                              20

<210> SEQ ID NO 18
<211> LENGTH: 26
<212> TYPE: DNA
<213> ORGANISM: Artificial Sequence
<220> FEATURE:
<223> OTHER INFORMATION: Capturing probe

<400> SEQUENCE: 18
gaagtcaaca ggacgacgcc gcgcaa                                       26

<210> SEQ ID NO 19
<211> LENGTH: 47
<212> TYPE: DNA
<213> ORGANISM: Artificial Sequence
<220> FEATURE:
<223> OTHER INFORMATION: Nucleotide sequence of a certain target nucleic
      acid.  The 7th nucleotide (cytocine) is methylated at position 5.

<400> SEQUENCE: 19
aatcagcggg agctctttct ttgcgcggcg tccgtcctgt tgacttc                47

<210> SEQ ID NO 20
<211> LENGTH: 45
<212> TYPE: DNA
<213> ORGANISM: Artificial Sequence
<220> FEATURE:
<223> OTHER INFORMATION: Nucleotide sequence of a certain target nucleic
      acid.  The 2nd, 15th and 20th nucleotides (cytosines) are
      methylated at position 5.

<400> SEQUENCE: 20
gcggagctct ccctcgggac ggtggcagcc tcgagtggtc ctgca                  45

<210> SEQ ID NO 21
<211> LENGTH: 44
<212> TYPE: DNA
<213> ORGANISM: Artificial Sequence
<220> FEATURE:
<223> OTHER INFORMATION: Capturing probe
```

```
<400> SEQUENCE: 21
aaaaaaaaaa aaaaaaaaaa tgcaggacca ctcgaggctg ccac          44

<210> SEQ ID NO 22
<211> LENGTH: 24
<212> TYPE: DNA
<213> ORGANISM: Artificial Sequence
<220> FEATURE:
<223> OTHER INFORMATION: Capturing probe

<400> SEQUENCE: 22
tgcaggacca ctcgaggctg ccac                                24

<210> SEQ ID NO 23
<211> LENGTH: 44
<212> TYPE: DNA
<213> ORGANISM: Artificial Sequence
<220> FEATURE:
<223> OTHER INFORMATION: Nucleotide sequence of a certain target nucleic
      acid.  The 2nd, 7th, 13th, 34th and 39th nucleotides (cytosines)
      are methylated at position 5.

<400> SEQUENCE: 23
gcgcaccgtt tgcgacttgg tgagtgtctg ggtcgcctcg ctcc          44

<210> SEQ ID NO 24
<211> LENGTH: 40
<212> TYPE: DNA
<213> ORGANISM: Artificial Sequence
<220> FEATURE:
<223> OTHER INFORMATION: Capturing probe

<400> SEQUENCE: 24
aaaaaaaaaa aaaaaaaaaa acccagacac tcaccaagtc               40

<210> SEQ ID NO 25
<211> LENGTH: 20
<212> TYPE: DNA
<213> ORGANISM: Artificial Sequence
<220> FEATURE:
<223> OTHER INFORMATION: Capturing probe

<400> SEQUENCE: 25
acccagacac tcaccaagtc                                     20

<210> SEQ ID NO 26
<211> LENGTH: 46
<212> TYPE: RNA
<213> ORGANISM: Artificial Sequence
<220> FEATURE:
<223> OTHER INFORMATION: Heterologous nucleic acid probe for capturing
      the target nucleic acid of SEQ ID NO:11.  The first region from
      1th to 26th nucleotide residues is composed of 2'-O-methylated RNA
      and the second region from 27th to 48th nucleotide residues is
      composed

<400> SEQUENCE: 26
gaagucaaca ggacgacgcc gcgcaaaaaa aaaaaaaaaa aaaaaa        46
```

METHOD FOR MEASURING MODIFIED NUCLEOBASE USING SOLID PHASE PROBE, AND KIT FOR SAME

TECHNICAL FIELD

The present invention relates to a method and a kit for measuring a modified nucleobase.

BACKGROUND ART

Many techniques that detect nucleobases to which substances such as biotin are artificially introduced by immunoassays using antibodies in nucleic acid (e.g., DNA, RNA) detection have been reported. Techniques that detect naturally occurring modified nucleobases (e.g., methylcytosine, hydroxymethylcytosine) by immunoassays are also reported (Patent Literature 1, and Non Patent Literature 1 and 2).

PRIOR ART REFERENCE

Patent Literature

Patent Literature 1: Japanese Patent Application Laid-open No. 2012-230019

Non-Patent Literature

Non Patent Literature 1: Proll et al., DNA Research, 13, 37-42 (2006)
Non Patent Literature 2: Kurita et al., Anal. Chem., 2012, 84, 7533-7538

SUMMARY OF INVENTION

Problem to be Solved by the Invention

The inventors of the present invention have found out that in constructing the above immunoassay system that detects modified nucleobases, there is a problem in that a background value of a detection signal increases owing to non-specific binding of an antibody against a modified nucleobase to a nucleic acid probe. Consequently, a technique for suppressing the background value has been required to be developed in order to construct a high-sensitivity immunoassay system.

Means for Solving Problem

As a result of intensive investigations, the inventors of the present invention have succeeded in suppressing the background value and the like by using two kinds of probes (a capture probe and a solid phase probe) in combination in the measurement of a modified nucleobase in a target nucleic acid using an antibody against the modified nucleobase and have achieved the present invention.

That is, the present invention is as follows.

[1] A method for measuring a modified nucleobase, the method comprising:
(1) incubating a nucleic acid sample, a capture probe, and a solid phase probe in a solution; and
(2) measuring the modified nucleobase using an antibody against the modified nucleobase in the solution obtained at (1).
[2] The method according to [1], wherein the nucleic acid sample contains a target nucleic acid containing the modified nucleobase, and the steps (1) and (2) are performed by (1') and (2'), respectively:
(1') reacting the nucleic acid sample containing the target nucleic acid containing the modified nucleobase, the capture probe, and the solid phase probe in the solution by incubation to form a hybrid composed of the target nucleic acid, the capture probe, and the solid phase probe; and
(2') measuring the modified nucleobase using the antibody against the modified nucleobase in the solution containing the hybrid.
[3] The method according to [1] or [2], wherein the target nucleic acid is a target nucleic acid potentially containing two or more modified nucleobases.
[4] The method according to any one of [1] to [3], further comprising adding a solution containing the nucleic acid sample and the capture probe to a solid phase immobilized with the solid phase probe to prepare a solution containing the nucleic acid sample, the capture probe, and the solid phase probe.
[5] The method according to any one of [1] to [4], wherein the nucleic acid sample is a sample containing a target DNA containing a modified nucleobase.
[6] The method according to any one of [1] to [5], wherein either one or both of the capture probe and the solid phase probe is a probe containing a nucleic acid heterogeneous to the target nucleic acid.
[7] The method according to [6], wherein the capture probe is a probe containing a nucleic acid heterogeneous to the target nucleic acid.
[8] The method according to any one of [1] to [7], wherein the solid phase probe is poly A or poly T.
[9]. The method according to any one of [1] to [8], wherein a nucleobase that composes the modified nucleobase is cytosine.
[10] The method according to any one of [1] to [9], wherein the modified nucleobase is methylcytosine.
[11] The method according to any one of [2] to [10], wherein the capture probe is designed such that an unpaired part of the modified nucleobase is formed in a double-stranded structure part composed of the target nucleic acid and the capture probe in the hybrid.
[12] The method according to any one of [2] to [11], wherein the capture probe is designed such that the modified nucleobase is present in a single-stranded structure part of the hybrid.
[13] The method according to any one of [1] to [12], wherein the measurement of the modified nucleobase using the antibody against the modified nucleobase is performed by ELISA.
[14] A kit for measuring a modified nucleobase, the kit comprising:
(I) a capture probe;
(II) a solid phase probe; and (III) an antibody against the modified nucleobase.

Effect of Invention

The method and the kit of the present invention can measure a modified nucleobase in a target nucleic acid with high sensitivity by reducing a background value of a detection signal.

EMBODIMENTS FOR CARRYING OUT THE INVENTION

Figure 1:
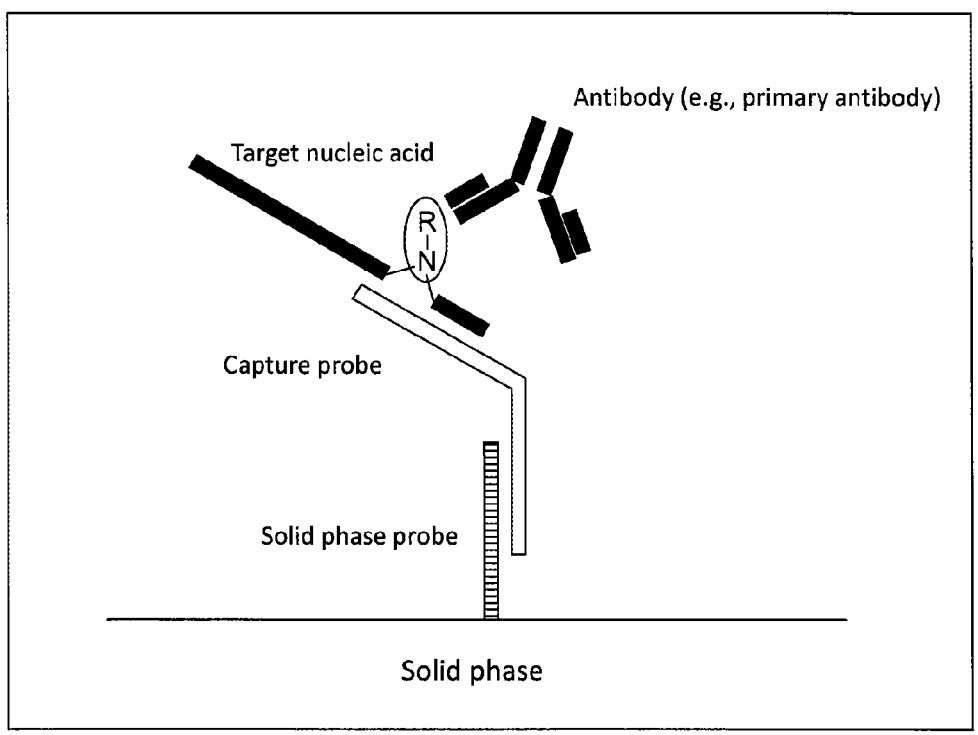
FIG. 1 is a diagram of an example of a measurement summary of a modified nucleobase in a target nucleic acid by the method of the present invention. R—N: a nucleotide residue having a modified nucleobase; N: a nucleotide residue having a nucleobase; and R: a substituent that a nucleobase has.

The present invention provides a method for measuring a modified nucleobase. The method of the present invention includes the following:
(1) incubating a nucleic acid sample, a capture probe, and a solid phase probe in a solution; and
(2) measuring the modified nucleobase using an antibody against the modified nucleobase in the solution obtained at (1).

The nucleic acid sample is a sample containing a target nucleic acid containing a modified nucleobase or a sample suspected to contain the target nucleic acid. The nucleic acid sample may also be an organism-derived biological sample, an environmental sample, or the like. Examples of the organism from which the biological sample is derived include animals such as mammals (e.g., humans, monkeys, mice, rats, rabbits, cattle, pigs, horses, goats, sheep) and birds (e.g., chickens), insects, microorganisms, plants, fungi, and fishes. The biological sample may also be a blood-related sample that is blood itself or a blood-derived sample (e.g., whole blood, blood serum, blood plasma), saliva, urine, milk, tissue or cell extract, or a combination thereof. The biological sample may further be derived from mammals contracting diseases (e.g., cancer, leukemia) or mammals that may contract diseases. Examples of the environmental sample include samples derived from soil, sea water, and fresh water that may contain nucleic acids. These samples may be subjected to another treatment before being used in the method of the present invention. Examples of the treatment include extraction and fragmentation (e.g., treatment with an enzyme such as a restriction enzyme) of nucleic acids (e.g., DNA such as genomic DNA, RNA). Consequently, the method of the present invention may further include extracting a nucleic acid from the nucleic acid sample and/or fragmenting the nucleic acid. The method of the present invention may also further include treating the sample by centrifugation, extraction, filtration, precipitation, heating, freezing, refrigeration, stirring, or the like.

The target nucleic acid is DNA or RNA, and DNA is preferable. The target nucleic acid is also a coding region or a non-coding region (e.g., a transcriptional regulation region) of DNA. The number of nucleotide residues composing the target nucleic acid (that is, the length of the target nucleic acid) is not limited to a particular number so long as it enables hybridization with the capture probe and may be 10 or more, preferably 15 or more, and more preferably 20 or more, for example. The number of nucleotides composing the target nucleic acid is also not limited to a particular number and may be any number that may occur by fragmentation of genomic DNA, for example. The number of the nucleotides composing the target nucleic acid may be 10,000 or less, 5,000 or less, 2,000 or less, 1,000 or less, 500 or less, 200 or less, or 100 or less, for example. A GC content of the target nucleic acid is not limited to a particular value and may be 10% or more, 20% or more, 30% or more, 40% or more, 50% or more, or 60% or more, for example. The GC content of the target nucleic acid is also 90% or less, 80% or less, or 70% or less, for example. The number of the modified nucleic acid that the target nucleic acid contains is not limited to a particular number so long as it is one or more (e.g., 1 to 100, 1 to 20, 1 to 10, or 1 to 5).

In the present invention, the modified nucleic acid refers to a nucleobase having a structure in which a normal nucleobase selected from the group consisting of adenine (A), guanine (G), cytosine (C), thymine (T), and uracil (U) is modified. When the target nucleic acid is DNA, examples of the term "nucleobase" in the expression "modified nucleobase" include adenine (A), guanine (G), cytosine (C), and thymine (T). When the target nucleic acid is RNA, examples thereof include adenine (A), guanine (G), cytosine (C), and uracil (U). The nucleobase is preferably cytosine (C). Examples of modification include introduction of a substituent to the normal nucleobase, elimination of a group (e.g., an amino group, an oxo group, a methyl group) that the normal nucleobase has, and exchange of a group that the normal nucleobase has with a substituent. The substituent is not limited to a particular type so long as it is one that naturally occurring nucleobases can have, and examples thereof include the substituents that the modified nucleobases in the modified nucleotides described in Administrative Instructions under the Patent Cooperation Treaty (the version enforced on Jan. 1, 2009), Annex C, Appendix 2, Table 2: List of Modified Nucleotides have. The modified nucleotides described in the literature can be the same as the modified nucleotides described in "Guidelines for Preparation of Specifications Containing Nucleotide Sequences or Amino Acid Sequences (July of 2002) or (December of 2009)," Annex 2, Table 2: Modified Base Table disclosed by the Japan Patent Office. Consequently, concerning the modified nucleobase, the guidelines can also be referred to. The substituent is preferably methyl, hydroxymethyl, or carboxy and more preferably methyl or hydroxymethyl. The position of the modification such as substitution is not limited to a particular position and is the 2-position or the 4- to 6-positions, for example, and preferably the 5-position for the nucleobase (C, T, or U) having a pyrimidine ring and is the 2-position, the 6-position, or the 8-position, for example, for the nucleobase (A or G) having a purine ring.

The modified nucleobase is not limited to a particular type so long as it can naturally occur, and examples thereof include the modified nucleobases that the modified nucleotides described in Administrative Instructions under the Patent Cooperation Treaty (the version enforced on Jan. 1, 2009), Annex C, Appendix 2, Table 2: List of Modified Nucleotides have. The modified nucleotides described in the literature can be the same as the modified nucleotides described in the guidelines, Annex 2, Table 2: Modified Base Table. Consequently, concerning the modified nucleobase, the guidelines can also be referred to. The modified nucleobase is preferably methylcytosine (e.g., 5-methylcytosine), hydroxymethylcytosine (e.g., 5-hydroxymethylcytosine), or carboxylcytosine (e.g., 5-carboxylcytosine). The modified nucleobase is more preferably methylcytosine (e.g., 5-methylcytosine) or hydroxymethylcytosine (e.g., 5-hydroxymethylcytosine). It is known that the modified nucleobase brings changes in functions of nucleic acids (e.g., a change in the transcriptional regulation capability of a certain gene).

The capture probe used in the present invention is a nucleic acid molecule that can hybridize with the target nucleic acid and the solid phase probe. The capture probe can hybridize with the target nucleic acid in a first region and can hybridize with the solid phase probe in a second region, for example. The capture probe can be composed of nucleic acids homogeneous and/or heterogeneous to the target nucleic acid. The term "homogeneous" means that the capture probe has the same backbone structure as a backbone structure (a structure composed of a sugar moiety and a phosphoric acid moiety) of the target nucleic acid as the whole of the backbone structure. The term "heterogeneous" means that the capture probe has a backbone structure different from the backbone structure (the structure composed of the sugar moiety and the phosphoric acid moiety) of the target nucleic acid as part or the whole of the backbone structure. Consequently, the type of the capture probe is determined in accordance with the type of the target nucleic acid. When the target nucleic acid is DNA, for example, a DNA probe can be used as the capture probe of the homogeneous nucleic acid, and a nucleic acid probe other than the DNA probe can be used as the capture probe of the heterogeneous nucleic acid. When the target nucleic acid is natural RNA, a normal RNA probe composed of RNA homogeneous with the natural RNA can be used as the capture probe of the homogeneous nucleic acid, and a nucleic acid probe other than the normal RNA probe can be used as the capture probe of the heterogeneous nucleic acid. The capture probe may preferably contain a nucleic acid heterogeneous to the target nucleic acid.

Examples of the capture probe include DNA probes, RNA probes, peptide nucleic acid (PNA) probes, locked nucleic acid (also called LNA or bridged nucleic acid (BNA)) probes, phosphorothioate (S—) nucleic acid probes, and chimera nucleic acid probes in which two or more such nucleic acid probes are coupled and/or mixed with each other (the chimera nucleic acid probe inevitably contains a nucleic acid heterogeneous to the target nucleic acid). Examples of the RNA probes include a normal RNA probe composed of a natural ribonucleotide having a hydroxy group at the 2'-position and a modified RNA probe composed of a ribonucleotide the 2'-position hydroxy group of which is modified. The modified RNA probe may be a ribonuclease-resistant RNA probe. Examples of the modified RNA probe include a 2'-O-alkylated RNA probe. The 2'-O-alkylated RNA probe is preferably 2'-O—$C_{1-6}$ alkylated RNA probe. The $C_{1-6}$ alkyl group of the $C_{1-6}$ alkylation is a linear, branched, or cyclic $C_{1-6}$ alkyl group, and examples thereof include a methyl group, an ethyl group, a propyl group (e.g., n-propyl, iso-propyl), a butyl group (e.g., n-butyl, iso-butyl, sec-butyl, tert-butyl), a pentyl group, and a hexyl group. In terms of easiness of manufacture and acquisition or the like, the 2'-O—$C_{1-6}$ alkylated RNA probe is preferably a 2'-O-methylated RNA probe.

The number of nucleotide residues composing the capture probe (that is, the length of the capture probe) is not limited to a particular number so long as it is long enough to be able to hybridize with the target nucleic acid and the solid phase probe and may be 20 or more, preferably 25 or more, and more preferably 30 or more, for example. The number of nucleotides composing the capture probe may also be 100 or less, 80 or less, 60 or less, or 50 or less, for example. A GC content in the first region that can hybridize with the target nucleic acid in the capture probe is not limited to a particular value and may be 10% or more, 20% or more, 30% or more, 40% or more, 50% or more, or 60% or more, for example. The GC content in the first region may also be 90% or less, 80% or less, or 70% or less, for example. The second region that can hybridize with the solid phase probe in the capture probe may be composed of homogeneous nucleotide residues alone or two or more heterogeneous nucleotide residues. When the second region is composed of the homogeneous nucleotide residues alone and the capture probe is a DNA probe, the second region is preferably a poly A, poly G, or poly T region composed of nucleotide residues alone containing any one of adenine, guanine, or thymine alone as a nucleobase and more preferably a poly A or poly T region composed of nucleotide residues alone containing either adenine or thymine alone. When the second region is composed of the homogeneous nucleotide residues alone and the capture probe is an RNA probe, the second region is preferably a poly A, poly G, or poly U region composed of nucleotide residues alone containing any one of adenine, guanine, or uracil alone as a nucleobase and more preferably a poly A or poly U region composed of nucleotide residues alone containing either adenine or uracil alone. The second region is preferably a poly A or poly T region. The capture probe can be prepared by a method of synthesizing a probe known in the relevant field, for example. The capture probe is used in the form of being free.

In the present invention, the solid phase probe refers to a probe that can hybridize with the capture probe and can be immobilized to a solid phase. The solid phase probe is used in the form of being free or the form of being immobilized to the solid phase (described below) at the step (1). Consequently, the solid phase probe may be labeled with a substance or group that enables immobilization to the solid phase. The labeling is performed either at the 5'-end or the 3'-end, for example. Examples of the substance or group that enables immobilization to the solid phase include substances or groups that enable covalent binding to the solid phase and affinity substances. Examples of the substances or groups that enable covalent binding to the solid phase include a thiol group or substances having a thiol group (the thiol group introduced into the solid phase probe can bind to a maleimide group on the solid phase) and an amino group or substances having an amino group (the amino group introduced into the solid phase probe can bind to maleic anhydride on the solid phase). Examples of the affinity substances include streptavidin, biotin, digoxigenin, dinitrophenol, fluorescein, and fluorescein isothiocyanate. In this case, a solid phase coated with another affinity substance having affinity with the affinity substance that the solid phase probe has can be used.

The solid phase probe can be composed of a nucleic acid homogeneous or heterogeneous to the target nucleic acid. The term "homogeneous" means that the solid phase probe has the same backbone structure as a backbone structure (a structure composed of a sugar moiety and a phosphoric acid moiety) of the target nucleic acid. The term "heterogeneous" means that the solid phase probe has a backbone structure different from the backbone structure (the structure composed of the sugar moiety and the phosphoric acid moiety) of the target nucleic acid. Consequently, the type of the solid phase probe is determined in accordance with the type of the target nucleic acid. When the target nucleic acid is DNA, for example, a DNA probe can be used as the solid phase probe of the homogeneous nucleic acid, and a nucleic acid probe other than the DNA probe can be used as the solid phase probe of the heterogeneous nucleic acid. When the target nucleic acid is natural RNA, a normal RNA probe composed of RNA homogeneous with the natural RNA can be used as the solid phase probe of the homogeneous nucleic acid, and a nucleic acid probe other than the normal RNA probe can be used as the solid phase probe of the heterogeneous nucleic acid. The solid phase probe may be preferably composed of a nucleic acid heterogeneous to the target nucleic acid.

Examples of the solid phase probe include DNA probes, RNA probes, peptide nucleic acid (PNA) probes, locked nucleic acid (also called LNA or bridged nucleic acid (BNA)) probes, phosphorothioate (S—) nucleic acid probes, and chimera nucleic acid probes in which two or more such nucleic acid probes are coupled and/or mixed with each other. Examples of the RNA probes include those described above with respect to the capture probe.

The total number of nucleotide residues composing the solid phase probe (that is, the length of the solid phase probe) is not limited to a particular number so long as it is long enough to hybridize with the capture probe and ensure the distance of the target nucleic acid from the solid phase to which the solid phase probe is immobilized, for example, and may be 10 or more, preferably 15 or more, and more preferably 20 or more, for example. In the present invention, by ensuring the distance to the target nucleic acid (that is, the modified nucleotide detected in the present invention) from the solid phase, the modified nucleobase can be detected with high sensitivity. The total number of nucleotides composing the solid phase probe may also be 100 or less, 80 or less, 70 or less, or 60 or less, for example. The solid phase probe can be prepared by a method for polymerizing nucleotides known in the relevant field, for example.

The solid phase probe is a homopolynucleotide or a heteropolynucleotide.

The homopolynucleotide refers to a polynucleotide composed of homogeneous nucleotide residues alone. When the homopolynucleotide is a DNA probe, the homopolynucleotide is preferably poly A, poly C, or poly T composed of nucleotide residues alone containing any one of adenine, cytosine, or thymine alone as a nucleobase and more preferably poly A or poly T composed of nucleotide residues alone containing either adenine or thymine alone. When the homopolynucleotide is an RNA probe, the homopolynucleotide is preferably poly A, poly C, or poly U composed of nucleotide residues alone containing any one of adenine, cytosine, or uracil alone as a nucleobase and more preferably poly A or poly U composed of nucleotide residues alone containing either adenine or uracil alone. The homopolynucleotide is preferably poly A or poly T.

The heteropolynucleotide refers to a polynucleotide composed of two or more heterogeneous nucleotide residues. When the heteropolynucleotide is a DNA probe, the heteropolynucleotide is preferably composed of nucleotide residues containing adenine, cytosine, or thymine as a nucleobase and more preferably composed of nucleotide residues containing adenine or thymine. When the heteropolynucleotide is an RNA probe, the heteropolynucleotide is preferably composed of nucleotide residues containing adenine, cytosine, or uracil as a nucleobase and more preferably composed of nucleotide residues containing adenine or uracil.

At the step (1), the incubation is performed in an appropriate solution on the condition that, when the target nucleic acid is contained in the nucleic acid sample, a hybridization reaction of the capture probe (being free), the solid phase probe (being free or immobilized to the solid phase described below), and the target nucleic acid in the nucleic acid sample is made possible. As the solution, a buffer solution containing a salt (e.g., sodium citrate) and other components (e.g., a surfactant) can be used, for example. A hybridization temperature is 15° C. to 95° C., for example (preferably 25° C. to 65° C.)

The expression "incubating a nucleic acid sample, a capture probe, and a solid phase probe in a solution" about the step (1) intends that the nucleic acid sample, the capture probe, and the solid phase probe are incubated in a simultaneous or staggered manner such that a hybrid composed of the target nucleic acid (when the nucleic acid sample contains the target nucleic acid), the capture probe, and the solid phase probe will finally be formed.

Consequently, the expression specifically contains the following modes:

(1-1) incubating the nucleic acid sample, the capture probe, and the solid phase probe in the solution simultaneously;

(1-2) incubating the nucleic acid sample and the capture probe first (when the nucleic acid sample contains the target nucleic acid, an intermediate hybrid composed of the target nucleic acid and the capture probe is formed) and then further incubating a solution obtained by the incubation in combination with the solid phase probe (when the nucleic acid sample contains the target nucleic acid, a hybrid composed of the target nucleic acid, the capture probe, and the solid phase probe is formed); and (1-3) incubating the capture probe and the solid phase probe first (an intermediate hybrid composed of the capture probe and the solid phase probe is formed) and then further incubating a solution obtained by the incubation in combination with the nucleic acid sample (when the nucleic acid sample contains the target nucleic acid, a hybrid composed of the target nucleic acid, the capture probe, and the solid phase probe is formed).

When the nucleic acid sample does not contain the target nucleic acid, even when the nucleic acid sample, the capture probe, and the solid phase probe are incubated in the solution, a target hybrid composed of the target nucleic acid, the capture probe, and the solid phase probe is not formed. In this case, the modified nucleobase cannot be detected at the step (2) described below, but it can be determined that the modified nucleobase is not present in the nucleic acid sample.

When the nucleic acid sample contains the target nucleic acid not containing the modified nucleobase (in other words, the target nucleic acid containing non-modified nucleobases alone), by incubating the nucleic acid sample, the capture probe, and the solid phase probe in the solution, the target nucleic acid not containing the modified nucleobase, the capture probe, and the solid phase probe react with each other, whereby a hybrid composed of the target nucleic acid, the capture probe, and the solid phase probe is formed. In this case, the modified nucleobase cannot be detected at the step (2) described below, but it can be determined that the modified nucleobase is not present in the nucleic acid sample (even though the target nucleic acid is present) or, in other words, that a certain nucleobase in the target nucleic acid is not modified.

When the nucleic acid sample contains the target nucleic acid containing the modified nucleobase, by incubating the nucleic acid sample, the capture probe, and the solid phase probe in the solution, the target nucleic acid containing the modified nucleobase, the capture probe, and the solid phase probe react with each other, whereby a hybrid composed of the target nucleic acid, the capture probe, and the solid phase probe is formed. In this case, it can be determined that the modified nucleobase is present at the step (2) described below, and the modified nucleobase can also be quantified.

In the present invention, the hybrid is a hybridization complex composed of the target nucleic acid, the capture probe, and the solid phase probe and having a double-stranded structure of the target nucleic acid and the capture probe formed through hybridization between the target nucleic acid and the capture probe and a double-stranded structure of the capture probe and the solid phase probe formed through hybridization between the capture probe and the solid phase probe. Examples of the structure of the hybrid are as illustrated in the following Table 1-1 to Table 1-5. The double-stranded structure of the target nucleic acid and the capture probe may be formed at the entire region or a partial region of the target nucleic acid. The hybrid may have a single-stranded structure of the target nucleic acid either at a 5'-end region or 3'-end region [e.g., (a-1) to (a-5) and (b-1) to (b-5)] or may form the double-stranded structure across the entire region of the target nucleic acid [e.g., (c-1) to (c-5), (d-1) to (d-5), (e-1) to (e-5), and (f-1) to (f-5)], for example. The solid phase probe may hybridize with the capture probe at a 5'-end region to form the double-stranded structure [e.g., (a-1) to (a-2), (c-1) to (c-2), (e-1) to (e-2), (b-3) to (b-5), (d-3) to (d-5), and (f-3) to (f-5)] or may hybridize with the capture probe at a 3'-end region to form the double-stranded structure [e.g., (a-3) to (a-5), (c-3) to (c-5), (e-3) to (e-5), (b-1) and (b-2), (d-1) and (d-2), and (f-1) and (f-2)]. The single-stranded structure is a structure formed by including a non-hybridized region of one or more nucleotide residues at the 5'-end and/or the 3'-end of the target nucleic acid, the capture probe, or the solid phase probe forming the hybrid or a non-end of the capture probe. (a-1) to (f-5) present structures in which at least three end regions among the 5'-end region and the 3'-end region of the target nucleic acid, the 5'-end region and the 3'-end region of the capture probe, and the 5'-end region and the 3'-end region of the solid phase probe hybridize. However, in the hybrid, these three end regions are also not necessarily required to hybridize; both the 3'-end region of the target nucleic acid and the 5'-end region of the capture probe may have single-stranded structure parts (that is, non-hybridized regions), both the 5'-end region of the target nucleic acid and the 3'-end region of the capture probe may have single-stranded structure parts, both the 3'-end region of the capture probe and the 5'-end region of the solid phase probe may have single-stranded structure parts, and both the 5'-end region of the capture probe and the 3'-end region of the solid phase probe may have single-stranded structure parts.

TABLE 1-1

Examples of structure of hybrid (1)

| | | |
|---|---|---|
| Target nucleic acid | 5'-■■■■-3' | 5'-■■■■-3' |
| Capture probe | 3'-▭▭▭-5' | 3'-▭▭▭-5' |
| Solid phase probe | 5'-▥▥▥▥▥-3' 5'-▥▥▥▥▥-3' | |
| | (a-1) | (b-1) |

| | | |
|---|---|---|
| Target nucleic acid | 5'-■■-3' | 5'-■■-3' |
| Capture probe | 3'-▭▭▭-5' | 3'-▭▭▭-5' |
| Solid phase probe | 5'-▥▥▥▥▥-3' | 5'-▥▥▥▥▥-3' |
| | (c-1) | (d-1) |

TABLE 1-1-continued

Examples of structure of hybrid (1)

| | | |
|---|---|---|
| Target nucleic acid | 5'-■■-3' | 5'-■■-3' |
| Capture probe | 3'-☐-5' | 3'-☐-5' |
| Solid phase probe | 5'-▯▯▯▯▯▯▯▯-3' | 5'-▯▯▯▯▯▯-3' |
| | (e-1) | (f-1) |

TABLE 1-2

Examples of structure of hybrid (2)

| | | |
|---|---|---|
| Target nucleic acid | 5'-■■■-3' | 5'-■■-3' |
| Capture probe | 3'-☐-5' | 3'-☐-5' |
| Solid phase probe | 5'-▱▱▱╲ 3' | ╱▱▱▱-3'  5'-╱ |
| | (a-2) | (b-2) |

| | | |
|---|---|---|
| Target nucleic acid | 5'-■-3' | 5'-■■-3' |
| Capture probe | 3'-☐-5' | 3'-☐-5' |
| Solid phase probe | 5'-▱▱╲ 3' | ╱▱▱-3'  5'-╱ |
| | (c-2) | (d-2) |

| | | |
|---|---|---|
| Target nucleic acid | 5'-■■-3' | 5'-■■-3' |
| Capture probe | 3'-☐-5' | 3'-☐-5' |
| Solid phase probe | 5'-▱▱╲ 3' | ╱▱▱-3'  5'-╱ |
| | (e-2) | (f-2) |

TABLE 1-3

Examples of structure of hybrid (3)

| | | |
|---|---|---|
| Target nucleic acid | 5'-■■■-3' | 5'-■■■-3' |
| Capture probe | 3'-☐-5' | 3'-☐-5' |
| Solid phase probe | ╱▱▱-3'  5'-╱ | 5'-▱▱╲ 3' |
| | (a-3) | (b-3) |

| | | |
|---|---|---|
| Target nucleic acid | 5'-■■-3' | 5'-■■-3' |
| Capture probe | 3'-☐-5' | 3'-☐-5' |
| Solid phase probe | ╱▱▱-3'  5'-╱ | 5'-▱▱╲ 3' |
| | (c-3) | (d-3) |

| | | |
|---|---|---|
| Target nucleic acid | 5'-■■-3' | 5'-■■-3' |
| Capture probe | 3'-☐-5' | 3'-☐-5' |
| Solid phase probe | ╱▱▱-3'  5'-╱ | 5'-▱▱╲ 3' |
| | (e-3) | (f-3) |

TABLE 1-4

Examples of structure of hybrid (4)

(a-4) (b-4) (c-4) (d-4) (e-4) (f-4)

TABLE 1-5

Examples of structure of hybrid (5)

(a-5) (b-5) (c-5) (d-5) (e-5) (f-5)

In the hybrid, the number of nucleotide residues of the target nucleic acid and the capture probe corresponding to the double-stranded structure part of the target nucleic acid and the capture probe and the number of nucleotide residues of the capture probe and the solid phase probe corresponding to the double-stranded structure part of the capture probe and the solid phase probe (that is, the length of the double-stranded structure parts) are each not limited to a particular length so long as they are long enough to enable hybridization with the target nucleic acid and may be 10 or more, preferably 15 or more, and more preferably 20 or more, for example. The number of the nucleotide residues may also be 100 or less, 80 or less, 60 or less, 50 or less, 40 or less, or 30 or less, for example. A GC content in the double-stranded structure part of the target nucleic acid and the capture probe is not limited to a particular value and may be 10% or more, 20% or more, 30% or more, 40% or more, 50% or more, or 60% or more, for example. The GC content in the double-stranded structure part of the target nucleic acid and the capture probe may also be 90% or less, 80% or less, or 70% or less, for example. It is preferable that the GC content in the double-stranded structure part of the capture probe and the solid phase probe be low.

In the hybrid, the number of nucleotide residues of the target nucleic acid, the capture probe, and the solid phase probe corresponding to the single-stranded structure parts (that is, the length of each of the single-stranded structure parts) is not limited to a particular number so long as it is one or more and is two or more, three or more, four or more, five or more, six or more, seven or more, eight or more, nine or more, 10 or more, 15 or more, 20 or more, or 50 or more, for example. The number is not limited to a particular number and may be 10,000 or less, 5,000 or less, 2,000 or less, 1,000 or less, 500 or less, 200 or less, or 100 or less, for example. The capture probe and/or the solid phase probe may be designed such that the single-stranded structure part will be formed at the 5'-end region or the 3'-end region in the hybrid.

In an embodiment, the capture probe may be designed such that an unpaired part of the modified nucleobase will be formed in the double-stranded structure part composed of the target nucleic acid and the capture probe in the hybrid. The unpaired part of the modified nucleobase can be introduced to facilitate detection of the modified nucleobase by an antibody. To form the unpaired part, a capture probe having a nucleotide sequence that is not perfectly complementary with respect to the target nucleic acid in the double-stranded structure part may be used, for example.

An example of the capture probe in which the unpaired part of the modified nucleobase is formed in the double-stranded structure part composed of the target nucleic acid and the capture probe in the hybrid is a capture probe lacking a nucleotide residue complementary with respect to a nucleotide residue having a modified nucleobase in the target nucleic acid [e.g., (I) in Table 2]. The capture probe may be a capture probe lacking one nucleotide residue alone complementary with respect to the nucleotide residue having the modified nucleobase in the target nucleic acid [e.g., (I-1) in Table 2] or a capture probe lacking two or more (2 to 20, 2 to 10, or 2 to 5, for example) adjacent nucleotide residues containing the nucleotide residue having the modified nucleobase in the target nucleic acid [e.g., (I-2) in Table 2]. The number of the nucleotide residue having the modified nucleobase in the unpaired part is not limited to a particular number so long as it is one or more as described above. Concerning the nucleic acid probe, refer to Patent Literature 1 and Non Patent Literature 2, for example. When the position of the nucleotide residue having the modified nucleobase in the target nucleic acid to be measured is determined, such design is made possible.

R—N: Nucleotide residue having modified nucleobase
N: Nucleotide residue having non-modified nucleobase composing target nucleic acid
N': Nucleotide residue composing capture probe
n in Nn: Number of nucleotide residues in bulge (loop) part (e.g., 2 to 20. When n is 2, either N1 or N2 or both N1 and N2 may have substituent R.)
R: Substituent that nucleobase has Another example of the capture probe in which the unpaired part of the modified nucleobase is formed in the double-stranded structure part composed of the target nucleic acid and the capture probe in the hybrid is a capture probe having a nucleotide residue noncomplementary with respect to the nucleotide residue having the modified nucleobase in the target nucleic acid [e.g., (I') in Table 2]. The capture probe may be a capture probe having one nucleotide residue alone noncomplementary with respect to the nucleotide residue having the modified nucleobase in the target nucleic acid [e.g., (I'-1) in Table 2] or a capture probe in which two or more (2 to 20, 2 to 10, or 2 to 5, for example) adjacent nucleotide residues including the nucleotide residue having the modified nucleobase in the target nucleic acid are noncomplementary [e.g., (I'-2) in Table 2]. When the position of the nucleotide residue having the modified nucleobase in the target nucleic acid to be measured is determined, such design is made possible.

TABLE 2

Formation of unpaired part of modified nucleobase in double-stranded structure part composed of target nucleic acid and capture probe in hybrid (1)

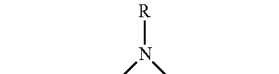

(I)

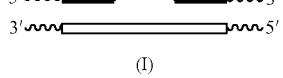

(I-1)

(I-2)

TABLE 3

Formation of unpaired part of modified nucleobase in double-stranded structure part composed of target nucleic acid and capture probe in hybrid (2)

(I')

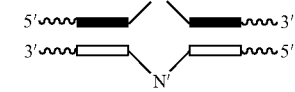

(I'-1)

(I'-2)

R—N: Nucleotide residue having modified nucleobase
N: Nucleotide residue having non-modified nucleobase composing target nucleic acid
N': Nucleotide residue composing capture probe
m in Nm: Number of nucleotide residues in noncomplementary part (N1 to Nm) (e.g., 2 to 20. When m is 2, either N1 or N2 or both N1 and N2 may have substituent R.)

m' in N'm': Number of nucleotide residues in noncomplementary part (N'1 to N'm') (e.g., 2 to 20)
R: Substituent that nucleobase has In another embodiment, the capture probe may be designed such that the modified nucleobase will be present in the single-stranded structure part of the hybrid. In the single-stranded structure part (the target nucleic acid) of the hybrid, the modified nucleobase may be present at a non-end part of the single-stranded structure part on the 5'-end side [e.g., (II) in Table 4], may be present at an end part of the single-stranded structure part on the 5'-end side [e.g., (III) in Table 4], may be present at a non-end part of the single-stranded structure part on the 3'-end side [e.g., (IV) in Table 4], may be present at an end part of the single-stranded structure part on the 3'-end side [e.g., (V) in Table 4], or may be any combination of two, three, or four of these. The capture probe may be designed such that the single-stranded structure part (the target nucleic acid) of the hybrid will contain the modified nucleobase in such a manner. The number of the nucleotide residue having the modified nucleobase in the single-stranded structure part is not limited to a particular number so long as it is one or more as described above. Alternatively, the capture probe may be designed such that the modified nucleobase will be present in the single-stranded structure part of the hybrid and that the unpaired part of the modified nucleobase will further be formed in the double-stranded structure part of the hybrid as described above. When the position of the nucleotide residue having the modified nucleobase in the target nucleic acid to be measured is determined, such design is made possible.

taining the modified nucleobase, the concentration of the target nucleic acid in the solution is not limited to a particular value so long as it is detectable by the method of the present invention and may be 0.01 nM or more, preferably 0.1 nM or more, more preferably 1 nM or more, 5 nM or more, or 10 nM or more, for example. The concentration of the target nucleic acid in the solution may also be 1 M or less, 100 mM or less, 10 mM or less, 1 mM or less, 100 µM or less, 10 µM or less, or 1 µM or less, for example. Since The concentration of the target nucleic acid in the nucleic acid sample is unknown in many cases, it may be difficult to strictly set a concentration of the target nucleic acid. Depending on the type of the nucleic acid sample, the concentration of the target nucleic acid that can be contained in the nucleic acid sample can empirically be predicted to some extent, or the concentration of the target nucleic acid is determined (in a case when although the size and/or concentration of the target nucleic acid is separately measured, the presence or absence of the modified nucleobase in the target nucleic acid and the content of the modified nucleobase in the target nucleic acid are unknown, for example). In such cases, setting of the concentration of the target nucleic acid may be attempted as described above.

The concentration of the capture probe in the solution is not limited to a particular value so long as the target nucleic acid is detectable by the method of the present invention and may be 0.01 nM or more, preferably 0.1 nM or more, more preferably 1 nM or more, further preferably 5 nM or more, and particularly preferably 10 nM or more, for example. The concentration of the capture probe in the solution may also

TABLE 4

Presence of modified nucleobase in single-stranded structure part of hybrid

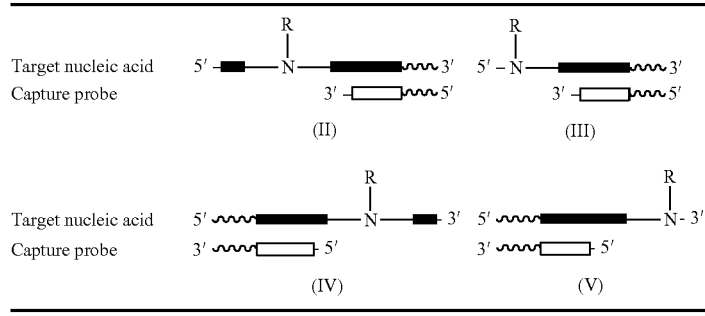

R—N: Nucleotide residue having modified nucleobase
N: Nucleotide residue having non-modified nucleobase
R: Substituent that nucleobase has The method of the present invention may further include adding a solution containing the nucleic acid sample and the capture probe to a solid phase immobilized with the solid phase probe to prepare a solution containing the nucleic acid sample, the capture probe, and the solid phase probe. In this case, the method of the present invention may further include adding the capture probe to a solution containing the nucleic acid sample to prepare a solution containing both the nucleic acid sample and the capture probe. The capture probe can be added to the nucleic acid sample in the form of a solid or as a solution. Alternatively, the method of the present invention may further include adding the nucleic acid sample and the capture probe simultaneously or separately to the solid phase probe in the solution immobilized to the solid phase to prepare a solution containing the nucleic acid sample, the capture probe, and the solid phase probe.

When the solution for incubation is prepared from the nucleic acid sample containing the target nucleic acid conbe 1 M or less, 100 mM or less, 10 mM or less, 1 mM or less, 100 µM or less, 10 µM or less, or 1 µM or less, for example. Consequently, the capture probe may be added to the solution such that such a concentration will be achieved.

The concentration of the solid phase probe in the solution is not limited to a particular value so long as the target nucleic acid is detectable by the method of the present invention and may be 0.01 nM or more, preferably 0.1 nM or more, and more preferably 1 nM or more, 5 nM or more, or 10 nM or more, for example. The concentration of the capture probe in the solution may also be 1 M or less, 100 mM or less, 10 mM or less, 1 mM or less, 100 µM or less, 10 µM or less, or 1 µM or less, for example. Consequently, the solid phase probe may be added to the solution such that such a concentration will be achieved.

In a preferable embodiment, the target nucleic acid may be a target nucleic acid potentially containing two or more modified nucleobases. The number of the modified nucleobases potentially contained in the target nucleic acid is not limited to a particular number so long as it is two or more and is 2 to 30, 2 to 20, 2 to 10, or 2 to 5 (e.g., 2, 3, 4, or 5), for example. When a plurality of modified nucleobases are contained in the target nucleic acid, it has been revealed that even when the concentration of the target nucleic acid in the solution used for the hybridization of the target nucleic acid and a heterogeneous nucleic acid probe is extremely low (e.g., 0.01 nM or more), the modified nucleobases can be measured with high sensitivity (Examples 6 and 7). Consequently, the method of the present invention can use a heterogeneous nucleic acid probe that is designed so as to hybridize with the target nucleic acid potentially containing two or more modified nucleobases. When the number of nucleobases potentially modified in the target nucleic acid to be measured is determined, such design is made possible.

The modified nucleobase is measured using an antibody against the modified nucleobase in a solution containing the hybrid. In the measurement, although the solution obtained at the step (1) may be used as it is, addition of another solution and/or replacement of the solution with another solution may be performed in order to perform measurement in a solution more suitable for the measurement of the modified nucleobase by the antibody. The replacement can be performed by adding the solution obtained at the step (1) to a solid phase, immobilizing the hybrid that can be contained in the solution to the solid phase, removing the solution from the solid phase, washing the solid phase with a cleaning liquid as needed, and adding another solution (e.g., a solution containing the antibody against the modified nucleobase) thereto, for example. The solution used in the measurement is not limited to a particular type so long as it is a solution suitable for an antigen-antibody reaction.

The measurement can be performed by immunological methodology. Examples of the immunological methodology include an enzyme immunoassay (EIA) (e.g., direct competitive ELISA, indirect competitive ELISA, and sandwich ELISA), a radioimmunoassay (RIA), a fluoroimmunoassay (FIA), immunochromatography, a luminescence immunoassay, a spin immunoassay, Western blot, and latex agglutination.

The antibody against the modified nucleobase may be a polyclonal antibody or a monoclonal antibody. The antibody against the modified nucleobase may be any isotype of immunoglobulin (e.g., IgG, IgM, IgA, IgD, IgE, IgY). The antibody against the modified nucleobase may be a full-length antibody. The full-length antibody refers to an antibody containing a heavy chain and a light chain, each of the chains containing a variable region and a constant region (e.g., an antibody containing two Fab parts and an Fc part). The antibody against the modified nucleobase may also be an antibody fragment derived from the full-length antibody. The antibody fragment is part of the full-length antibody, and examples thereof include F(ab')$_2$, Fab', Fab, and Fv. The antibody against the modified nucleobase may also be a modified antibody such as a single-stranded antibody. The antibody against the modified nucleobase may further be an antibody used as a primary antibody in an immunoassay such as ELISA, and in this case, a secondary antibody is used in combination.

The antibody against the modified nucleobase may have affinity for the modified nucleobase, a nucleoside having the modified nucleobase (a structural unit including the modified nucleobase and 2'-deoxyribose or ribose), a nucleotide having the modified nucleobase (a structural unit composed of the modified nucleobase, 2'-deoxyribose or ribose, and phosphate), or two or more nucleotides containing the nucleotide having the modified nucleobase (e.g., an oligonucleotide composed of two to five nucleotides). Examples of the antibody against the modified nucleobase when the target nucleic acid is DNA include 1) antibodies against a deoxyribonucleoside having a modified nucleobase selected from the group consisting of 2'-deoxy-modified adenosine, 2'-deoxy-modified guanosine, 2'-deoxy-modified cytidine, and 2'-deoxy-modified thymidine, 2) antibodies against a deoxyribonucleotide having a modified nucleobase selected from the group consisting of 2'-deoxy-modified adenosine 5'-phosphate, 2'-deoxy-modified guanosine 5'-phosphate, 2'-deoxy-modified cytidine 5'-phosphate, and 2'-deoxy-modified thymidine 5'-phosphate, and 3) antibodies against two or more deoxyribonucleotides containing the above deoxyribonucleotide having the modified nucleobase. Examples of the antibody against the modified nucleobase when the target nucleic acid is RNA include 1') antibodies against a nucleoside having a modified nucleobase selected from the group consisting of modified adenosine, modified guanosine, modified cytidine, and modified uridine, 2') antibodies against a ribonucleotide having a modified nucleobase selected from the group consisting of modified adenosine 5'-phosphate, modified guanosine 5'-phosphate, modified cytidine 5'-phosphate, and modified uridine 5'-phosphate and 3') antibodies against two or more ribonucleotides containing the above ribonucleotide having the modified nucleobase.

For the antibody against the modified nucleobase, an antibody prepared by using a complex of the modified nucleobase, the nucleoside having the modified nucleobase, the nucleotide having the modified nucleobase, or the two or more nucleotides containing the nucleotide having the modified nucleobase and a carrier protein (e.g., BSA, KLH) as an antigen can be used, for example. Since various antibodies against the modified nucleobase prepared using such complexes are commercially available, the method of the present invention may use a commercially available antibody, for example. The method of the present invention may also use the antibody against the modified nucleobase prepared as follows, for example.

The polyclonal antibody against the modified nucleobase can be acquired by administering the above complex as the antigen together with a commercially available adjuvant (e.g., a complete or incomplete Freund's adjuvant) to an animal subcutaneously or intra-abdominally about two to four times every 2 to 3 weeks, collecting whole blood about 3 to about 10 days after the final immunity, and purifying the antiserum, for example. Examples of the animal to which the antigen is administered include mammals such as rats, mice, rabbits, goats, cattle, guinea pigs, and hamsters.

The monoclonal antibody against the modified nucleobase can be prepared by cell fusion, for example. The above complex is administered together with a commercially available adjuvant to a mouse subcutaneously or intra-abdominally two to four times, collecting the spleen or a lymph node about three days after the final administration, and collecting white blood cells, for example. These white blood cells and a myeloma cell (e.g., NS-1) are subjected to cell fusion to obtain a hybridoma producing a monoclonal antibody against the factor. Examples of the cell fusion include a PEG method and a voltage pulse method. The hybridoma producing a desired monoclonal antibody can be selected by detecting an antibody that specifically binds to an antigen using known EIA, RIA, or the like in cultivated supernatant. Cultivation of the hybridoma producing the monoclonal antibody can be performed in vitro or in vivo such as in a mouse, a rat, or preferably mouse ascites, and the antibody can be acquired from the cultivated supernatant of the hybridoma or animal ascites. The monoclonal antibody may be any isotype of IgG, IgM, IgA, IgE, and the like. Alternatively, in vitro methods such as a phage display method (Ulman et al, Proc. Natl. Acad. Sci. U.S.A., 90, 1184-89 (1993)) and an ADLib system (WO2004/011644) are also known as methods for preparing a monoclonal antibody, and such methods may be used to prepare the antibody against the modified nucleobase.

The antibody against the modified nucleobase may be used while being immobilized to a solid phase. Examples of the solid phase include supports such as particles (e.g., magnetic particles), membranes (e.g., a nitrocellulose membrane), glass, plastic, and metal, containers such as plates (e.g., a multiwell plate), and devices. The antibody may also be provided in the form of being impregnated into a medium such as filter paper. The antibody against the modified nucleobase may be labeled with a labeling substance. Examples of the labeling substance include enzymes (e.g., peroxidase, alkaline phosphatase, luciferase, β-galactosidase), affinity substances (e.g., streptavidin, biotin), fluorescent substances or proteins (e.g., fluorescein, fluorescein isothiocyanate, rhodamine, green fluorescent protein, red fluorescent protein), luminescent substances (e.g., luciferin, aequorin), and radioactive substances (e.g., $^3$H, $^{14}$C, $^{32}$P, $^{35}$S, $^{125}$I). When a secondary antibody is used in the method of the present invention, the secondary antibody may be labeled with such a labeling substance.

The measurement of the modified nucleobase by the antibody against the modified nucleobase is performed qualitatively or quantitatively, and the presence or absence or the amount of the modified nucleobase can be evaluated. In the present invention, the measurement of the modified nucleobase intends not only the measurement of the modified nucleobase itself but also the measurement of the target nucleic acid containing the modified nucleobase.

The measurement of the presence or absence of the modified nucleobase may be perfumed as follows, for example:

(2-1) in the solution obtained at the step (1), performing an assay using the antibody against the modified nucleobase to measure a signal value;

(2-2) in a solution that does not contain the target nucleic acid containing the modified nucleobase and contains the capture probe and the solid phase probe, performing an assay using the antibody against the modified nucleobase to measure a background value; and (2-3) comparing the signal value with the background value to evaluate the presence or absence of the modified nucleobase.

In the measurement of the modified nucleobase, the signal value and the background value are values (e.g., absorbance, the degree of fluorescence, the degree of coloration, and radioactivity) that are measured using a label binding to the antibody against the modified nucleobase or the secondary antibody (when the secondary antibody is used).

The measurement of the amount of the modified nucleobase may be performed together with the measurement of the background value, for example. Specifically, the measurement of the amount of the modified nucleobase may be performed as follows:

(2-1') in the solution obtained at the step (1), performing an assay using the antibody against the modified nucleobase to measure a signal value;

(2-2') in a solution that does not contain the target nucleic acid containing the modified nucleobase and contains the capture probe and the solid phase probe, performing an assay using the antibody against the modified nucleobase to measure a background value;

(2-3') correcting the signal value with the background value to obtain a corrected signal value; and (2-4') based on the corrected signal value, evaluating the amount of the modified nucleobase.

Alternatively, the measurement of the amount of the modified nucleobase may be performed using a preparation. Specifically, the measurement of the amount of the modified nucleobase may be performed as follows:

(2-1") in the solution obtained at the step (1), performing an assay using the antibody against the modified nucleobase to measure a signal value;

(2-2") in a solution containing the target nucleic acid containing the modified nucleobase (preparation), the capture probe, and the solid phase probe, performing an assay using the antibody against the modified nucleobase to measure a value for calibration; and (2-3") comparing the signal value with the value for calibration to evaluate the amount of the modified nucleobase.

The above measurement using the preparation may be performed in combination with the above measurement of the background value.

In a specific embodiment, the method of the present invention may be performed by ELISA. When the nucleic acid sample contains the target nucleic acid containing the modified nucleobase, for example, the method of the present invention by ELISA may be performed as follows:

(i) incubating the nucleic acid sample containing the target nucleic acid containing the modified nucleobase, the capture probe, and a solid probe labeled with a first affinity substance in a solution to form a hybrid composed of the target nucleic acid, the capture probe, and the solid phase probe;

(ii) immobilizing the hybrid to a solid phase treated with a second affinity substance;

(iii) reacting a primary antibody against the modified nucleobase with the hybrid immobilized to the solid phase to obtain a primary complex of the primary antibody and the hybrid;

(iv) reacting a secondary antibody labeled with a labeling substance with the primary complex to obtain a secondary complex of the secondary antibody and the primary antibody; and (v) using the labeling substance that the secondary antibody in the secondary complex has, measuring the presence and/or the amount of the formed hybrid (in other words, the modified nucleobase).

The first affinity substance and the second affinity substance are used in a combination having mutual affinity (e.g., a combination of biotin and streptavidin). The method of the present invention may include (i') incubating the nucleic acid sample containing the target nucleic acid containing the modified nucleobase, the capture probe, and the solid phase probe immobilized to a solid phase in a solution to form a hybrid composed of the target nucleic acid, the capture probe, and the solid phase probe in place of the steps (i) and (ii). In this case, obtaining the solid phase probe immobilized to the solid phase (e.g., adding the solid phase probe labeled with the first affinity substance to the solid phase treated with the second affinity substance) may further be included. The method of the present invention may also include washing the solid phase before the step (iii). The secondary antibody may be an antibody that recognizes the primary antibody alone (e.g., an antibody that binds to the constant region of the primary antibody) and may also be an antibody that recognizes both the primary antibody in the secondary complex and the primary complex. In addition, the method of the present invention including (i) to (v) can be performed in accordance with the methodology described in detail in the specification.

The present invention also provides a kit for measuring a modified nucleobase. The kit of the present invention includes the following, for example:
(I) a capture probe;
(II) a solid phase probe; and
(III) an antibody against a modified nucleobase The capture probe, the solid phase probe, and the antibody against a modified nucleobase are as described above. The solid phase probe may be labeled with an affinity substance, and the antibody against a modified nucleobase may be labeled with a labeling substance, for example. The kit of the present invention may further contain the components as described above including the affinity substance, the labeling substance, the secondary antibody, a detection reagent for the secondary antibody (e.g., when the secondary antibody is labeled with an enzyme, a substrate for the enzyme), and the solid phase. The solid phase may be treated with the affinity substance. The kit of the present invention may also contain the preparation of the modified nucleobase or the preparation of the target nucleic acid containing the modified nucleobase as solution or as powder.

The kit of the present invention contains the components in the form of being isolated from each other or in the form of being mixed with each other. In the kit of the present invention, the components may be provided in the form of being contained in different containers (e.g., a tube, a plate), for example. The capture probe and the solid phase probe may be provided in the form of being mixed with each other (e.g., in the same solution), for example. Alternatively, the kit of the present invention may be provided in the form of a device. Specifically, all the components may be provided in the form of being contained in a device. Alternatively, part of the components may be provided in the form of being contained in a device, whereas the rest may be provided in the form of not being contained in the device (e.g., the form of being contained in a different container). In this case, the components not contained in the device may be used by being injected into the device in the measurement of a target substance.

EXAMPLES

Although the following describes the present invention in more detail with reference to examples, the present invention is not limited to these examples.

Example 1

Investigation of Solid Phase Probe

The effect of the solid phase probe on the background value of a detection signal was investigated.

The nucleotide sequences of the solid phase probes (DNA) are as listed in Table 5; those artificially synthesized by Hokkaido System Science Co., Ltd. were used.

TABLE 5

Table 5. Nucleotide sequence of solid phase probe

| Solid phase probe | Length | Nucleotide sequence (SEQ ID NO) |
|---|---|---|
| 1 | 20 | 5'-TTTTTTTTTTTTTTTTTTTT-3' (SEQ ID NO: 1) |
| 2 | 40 | 5'-TTTTTTTTTTTTTTTTTTTTTTTTTTTTTTTTTTTTTTTT-3' (SEQ ID NO: 2) |
| 3 | 20 | 5'-AAAAAAAAAAAAAAAAAAAA-3' (SEQ ID NO: 3) |
| 4 | 20 | 5'-GGGGGGGGGGGGGGGGGGGG-3' (SEQ ID NO: 4) |
| 5 | 20 | 5'-CCCCCCCCCCCCCCCCCCCC-3' (SEQ ID NO: 5) |
| 6 | 40 | 5'-CCCCCCCCCCCCCCCCCCCCCCCCCCCCCCCCCCCCCCCC-3' (SEQ ID NO: 6) |
| 7 | 40 | 5'-CCCCCTAGAAAATTGAGAGAAGTCCACCACAAAAAAAAAA-3' (SEQ ID NO: 7) |
| 8 | 41 | 5'-CACTGAACAAATGGCACTAGTAAACTGAGCCAAAAAAAAAA-3' (SEQ ID NO: 8) |
| 9 | 26 | 5'-GAAGTCAACAGGACGACGCCGCGCAA-3' (SEQ ID NO: 9) |
| 10 | 27 | 5'-GAAGTCAACAGGACGGACGCCGCGCAA-3' (SEQ ID NO: 10) |

First, 5 pmol of the solid phase probe was dissolved in 100 μL of a hybridization buffer (4×SSC, 0.1% SDS), and the whole amount thereof was added to a streptavidin-coated plate (manufactured by Thermo Scientific) and was reacted at 37° C. for 30 minutes to immobilize the solid phase probe on the streptavidin plate. The streptavidin plate was washed twice with 300 μL of PBS-T, and 500 ng/mL of an anti-methylcytosine antibody (Clone33D3 manufactured by Millipore Corporation. This antibody is an antibody that recognizes not only 5-methylscytosine but also at least part of a backbone structure of DNA (e.g., a structure composed of a repeating unit of a deoxyribose moiety and a phosphoric acid moiety)) was added thereto by 50 μL each and was reacted at 37° C. for 1 hour. The streptavidin plate was washed three times with 300 μL of PBS-T, and 500 ng/mL of a peroxidase-labeled anti-IgG antibody (manufactured by Thermo Scientific) was added thereto by 50 μL each and was reacted at 37° C. for 30 minutes. After the streptavidin plate was washed three times with 300 μL of PBS-T, 3,3',5,5'-tetramethylbenzidine was added thereto by 100 μL each and was reacted in a dark place at room temperature for 7 minutes. Thereafter, a 2N hydrochloric acid solution was added thereto by 100 μL each, and absorbance at 450 nm was measured by a microplate reader (Arvo manufactured by PerkinElmer, Inc.).

Figure 2:
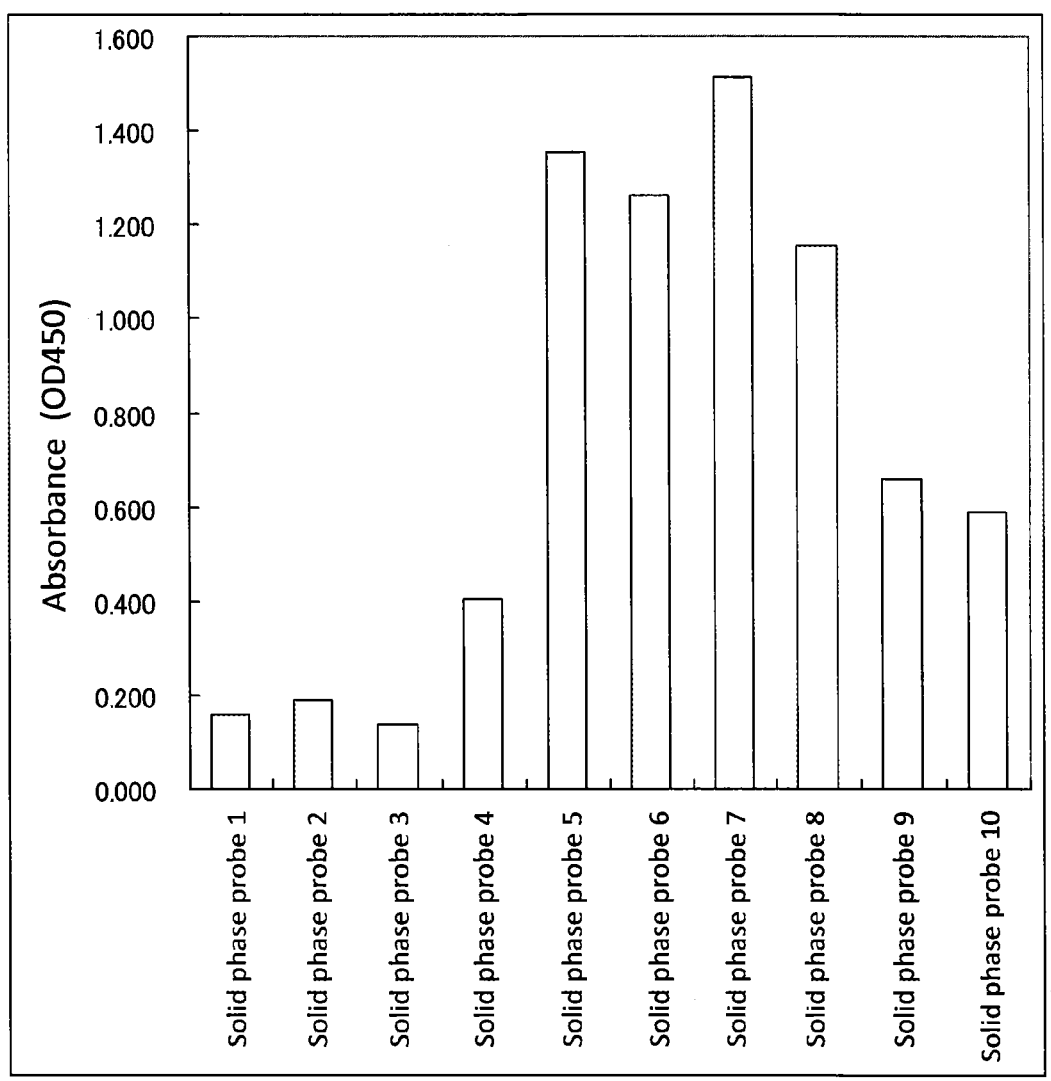
FIG. 2 is a diagram of signal values (background values) measured in the presence of Solid Phase Probes 1 to 10 and an antibody against a modified nucleobase.

As a result of the measurement, it was revealed that the background value of the detection signal substantially varied by the solid phase probe sequence (Table 6 and FIG. 2). From the result in Table 6, it was considered that the solid phase probe containing A and/or T (or U) (in other words, the solid phase probe not containing C and G) was preferable.

TABLE 6

Measurement of detection signal of solid phase probe

| Solid phase probe | OD450 |
|---|---|
| 1 | 0.160 |
| 2 | 0.191 |
| 3 | 0.139 |
| 4 | 0.403 |
| 5 | 1.355 |
| 6 | 1.261 |
| 7 | 1.513 |
| 8 | 1.155 |
| 9 | 0.657 |
| 10 | 0.590 |

Example 2

Use of Solid Phase Probe and Capture Probe in Measurement of Modified Nucleobase (1)

The nucleotide sequence of the target nucleic acid (DNA) is 5'-TTGCGCGGCGTC[C]GTCCTGTTGACTTC-3' (SEQ ID NO: 11, [C] is 5-methylcytosine), the nucleotide sequence of the capture probe (DNA) for capturing the target nucleic acid is 5'-GAAGTCAACAGGACGACGCCGCG-CAAAAAAAAAAAAAAAAAAAAAAA-3' (SEQ ID NO: 12), and the nucleotide sequence of the solid phase probe (DNA) is 5'-TTTTTTTTTTTTTTTTT-TTTTTTTTTTTTTTTTTTTTTT-3' (SEQ ID NO: 13, the 5'-end is biotin-labeled); those artificially synthesized by Hokkaido System Science Co., Ltd. were used. The capture probe was designed such that, when a hybrid of the target nucleic acid and the solid phase probe was formed, an unpaired part would be formed at the modified nucleobase [C] in the double-stranded structure part composed of the target nucleic acid and the capture probe.

The measurement of the modified nucleobase using the solid phase probe and the capture probe was carried out as follows. First, 5 pmol of the solid phase probe was dissolved in 100 μL of a PBS buffer solution, and the whole amount thereof was added to a streptavidin-coated plate (manufactured by Thermo Scientific) and was reacted at 37° C. for 30 minutes to immobilize the solid phase probe on the streptavidin plate. The immobilized solid phase probe nucleic acid was washed twice with 300 μL of PBS-T, and 100 μL of a solution containing the target nucleic acid containing 5-methylcytosine (1 pmol, 0.1 pmol, 0.01 pmol, or 0.001 pmol) and the capture probe (5 pmol) in a hybridization buffer (4×SSC, 0.1% SDS) was added thereto (in a nucleic acid sample solution, the concentration of the target nucleic acid was 10 nM, 1 nM, 0.1 nM, or 0.01 nM, the concentration of the capture probe was 50 nM, and the concentration of the solid phase probe was theoretically 50 nM or less (50 nM on the assumption that the whole amount of the solid phase probe used was immobilized to the solid phase)), was reacted at 60° C. for 2 hours, and was then reacted at 37° C. for 30 minutes to form a hybrid of three parties, that is, the target nucleic acid, the capture probe, and the solid phase probe. For a solution not containing the target nucleic acid, a similar operation was performed. The streptavidin plate was washed twice with 300 μL of PBS-T, and 500 ng/mL of the anti-methylcytosine antibody (Clone33D3 manufactured by Millipore Corporation) was added thereto by 50 μL each and was reacted at 37° C. for 1 hour. The streptavidin plate was washed three times with 300 μL of PBS-T, and 500 ng/mL of the peroxidase-labeled anti-IgG antibody (manufactured by Thermo Scientific) was added thereto by 50 μL each and was reacted at 37° C. for 30 minutes. After the streptavidin plate was washed three times with 300 μL of PBS-T, 3,3',5,5'-tetramethylbenzidine was added thereto by 100 μL each and was reacted in a dark place at room temperature for 7 minutes. Thereafter, a 2N hydrochloric acid solution was added thereto by 100 μL each, and absorbance at 450 nm was measured by the microplate reader (Arvo manufactured by PerkinElmer, Inc.).

Figure 3:
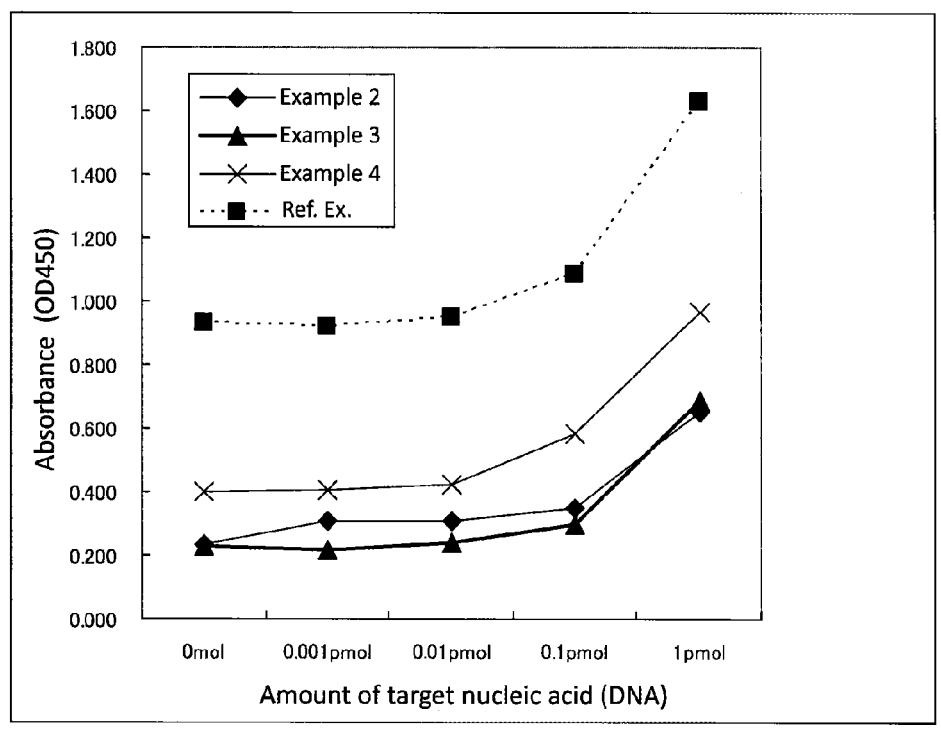
FIG. 3 is a diagram of signal values measured in measurement on the conditions of a target nucleic acid containing a modified nucleobase (0 mol, 0.001 pmol, 0.001 pmol, 0.1 mol, or 1 pmol), a capture probe (+), a solid phase probe (+: Examples 2 to 4; −: Reference Example 1), and an antibody against the modified nucleobase (+) (Examples 2 to 4 and Reference Example 1).
Figure 4:
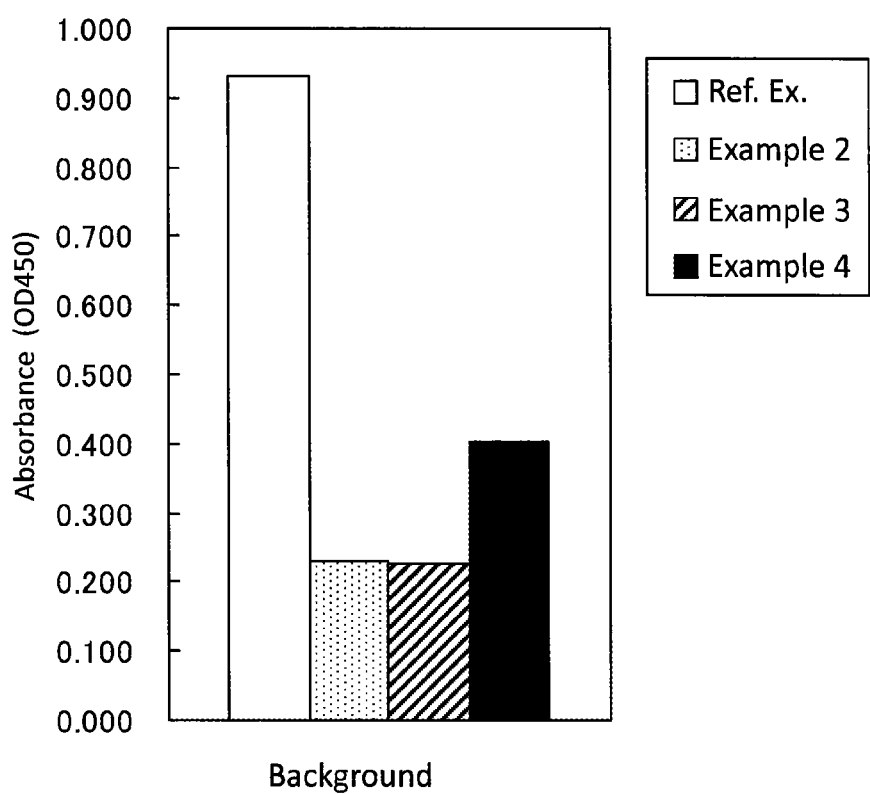
FIG. 4 is diagram of signal values (background values) measured in measurement on the conditions of the target nucleic acid containing the modified nucleobase (0 mol), the capture probe (+), the solid phase probe (+: Examples 2 to 4; −: Reference Example 1), and the antibody against the modified nucleobase (+).
Figure 5:
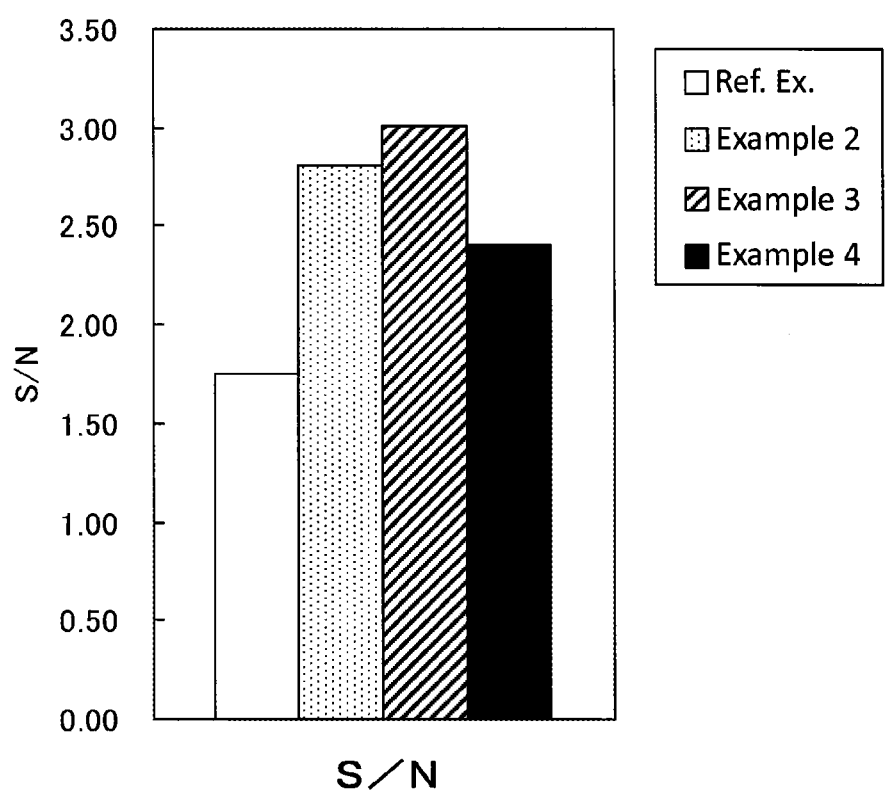
FIG. 5 is a diagram of signal-to-noise ratios (S/N) calculated in the measurement of the modified nucleobase (Examples 2 to 4 and Reference Example 1). In S/N, S indicates a signal value measured in measurement on the conditions of the target nucleic acid containing the modified nucleobase (1 pmol), the capture probe (+), the solid phase probe (+), and the antibody against the modified nucleobase (+), whereas N indicates a signal value (background value) measured in measurement on the conditions of the target nucleic acid containing the modified nucleobase (0 mol), the capture probe (+), the solid phase probe (+), and the antibody against the modified nucleobase (+).

As a result of the measurement, it was revealed that use of the solid phase probe and the capture probe in combination suppressed the background value and improved the S/N ratio compared with use of the capture probe alone (Reference Example 1) (Table 7, FIGS. 3 to 5).

Example 3

Use of Solid Phase Probe and Capture Probe in Measurement of Modified Nucleobase (2)

A test was carried out by a method similar to that in Example 2 except that 5'-GAAGTCAACAGGACGACGC-CGCGCAATTTTTTTTTTTTTTTTTTTTT-3' (SEQ ID NO: 14) and 5'-AAAAAAAAAAAAAAAAAAAAA-3' (SEQ ID NO: 15, the 5'-end is biotin-labeled) were used as the nucleotide sequence of the capture probe (DNA) and the nucleotide sequence of the solid phase probe (DNA), respectively.

As a result of the test, it was revealed that use of the solid phase probe and the capture probe in combination suppressed the background value and improved the S/N ratio compared with use of the capture probe alone (Reference Example 1) (Table 7, FIGS. 3 to 5).

Example 4

Use of Solid Phase Probe and Capture Probe in Measurement of Modified Nucleobase (3)

A test was carried out by a method similar to that in Example 2 except that 5'-GAAGTCAACAGGACGACGC-CGCGCAACCCCCCCCCCCCCCCCCCCCC-3' (SEQ ID NO: 16) and 5'-GGGGGGGGGGGGGGGGGGG-3' (SEQ ID NO: 17, the 5'-end is biotin-labeled) were used as the nucleotide sequence of the capture probe (DNA) and the nucleotide sequence of the solid phase probe (DNA), respectively.

As a result of the test, it was revealed that use of the solid phase probe and the capture probe in combination suppressed the background value and improved the S/N ratio compared with use of the capture probe alone (Reference Example 1) (Table 7, FIGS. 3 to 5). In addition, the solid phase probe and the capture probe used in the present example were lower in the efficiency of suppressing the background value than those of Example 2 and Example 3. This fact indicates that the solid phase probe in which the guanine residue content is lower is more appropriate.

Reference Example 1

Use of Capture Probe in Measurement of Modified Nucleobase (1)

The nucleotide sequence of the target nucleic acid (DNA) is 5'-TTGCGCGGCGTC[C]GTCCTGTTGACTTC-3' (SEQ ID NO: 11, [C] is 5-methylcytosine), and the nucleotide sequence of the capture probe (DNA) is 5'-GAAGT-CAACAGGACGACGCCGCGCAA-3' (SEQ ID NO: 18, the 5'-end is biotin-labeled); those artificially synthesized by Hokkaido System Science Co., Ltd. were used.

The measurement of the modified nucleobase using the capture probe was carried out as follows. First, the target nucleic acid containing 5-methylcytosine (1 pmol, 0.1 pmol, 0.01 pmol, or 0.001 pmol) and the probe nucleic acid (5 pmol) for capturing the target nucleic acid were dissolved in 100 µL of a hybridization buffer (4×SSC, 0.1% SDS) and were reacted at 60° C. for 2 hours to form a hybrid of the target nucleic acid and the probe nucleic acid for capturing the target nucleic acid. A solution not containing the target nucleic acid was also prepared, and a similar operation was performed. The solution after the hybridization reaction in an amount of 100 µL was added to a streptavidin-coated plate (manufactured by Thermo Scientific) and was reacted at 37° C. for 30 minutes to immobilize a nucleic acid hybrid on the streptavidin plate. The streptavidin plate was washed twice with 300 µL of PBS-T, and 500 ng/mL of the anti-methylcytosine antibody (Clone33D3 manufactured by Millipore Corporation) was added thereto by 50 µL each and was reacted at 37° C. for 1 hour. The streptavidin plate was washed three times with 300 µL of PBS-T, and 500 ng/mL of the peroxidase-labeled anti-IgG antibody (manufactured by Thermo Scientific) was added thereto by 50 µL each and was reacted at 37° C. for 30 minutes. After the streptavidin plate was washed three times with 300 µL of PBS-T, 3,3',5,5'-tetramethylbenzidine was added thereto by 100 µL each and was reacted in a dark place at room temperature for 7 minutes. Thereafter, a 2N hydrochloric acid solution was added thereto by 100 µL each, and absorbance at 450 nm was measured by the microplate reader (Arvo manufactured by PerkinElmer, Inc.).

The results were as listed and illustrated in Table 7 and FIGS. 3 to 5.

TABLE 7

| Methodology | | Target nucleic acid (DNA) | OD450 | S/N |
|---|---|---|---|---|
| Example 2 | Use of solid phase probe and capture probe in combination (two-step hybridization) | 1 pmol | 0.649 | 2.80 |
| | | 0.1 pmol | 0.349 | 1.50 |
| | | 0.01 pmol | 0.310 | 1.34 |
| | | 0.001 pmol | 0.310 | 1.34 |
| | | 0 mol | 0.232* | |
| Example 3 | | 1 pmol | 0.685 | 3.02 |
| | | 0.1 pmol | 0.296 | 1.30 |
| | | 0.01 pmol | 0.242 | 1.07 |
| | | 0.001 pmol | 0.217 | 0.96 |
| | | 0 mol | 0.227* | |
| Example 4 | | 1 pmol | 0.963 | 2.40 |
| | | 0.1 pmol | 0.585 | 1.46 |
| | | 0.01 pmol | 0.424 | 1.06 |
| | | 0.001 pmol | 0.404 | 1.01 |
| | | 0 mol | 0.401* | |
| Reference example 1 | Use of capture probe alone (one-step hybridization) | 1 pmol | 1.631 | 1.75 |
| | | 0.1 pmol | 1.085 | 1.17 |
| | | 0.01 pmol | 0.947 | 1.02 |
| | | 0.001 pmol | 0.918 | 0.99 |
| | | 0 mol | 0.930* | |

*Background value

Example 5

Use of Solid Phase Probe and Capture Probe in Measurement of Modified Nucleobase (4)

The nucleotide sequence of the target nucleic acid (DNA) is 5'-AATCAG[C]GGGAGCTCTTTCTTTGCGCG-GCGTCCGTCCTGTTGACTTC-3' (SEQ ID NO: 19, [C] is 5-methylcytosine), the nucleotide sequence of the capture probe (DNA) for capturing the target nucleic acid is 5'-GAAGTCAACAGGACGACGCCGCG-CAAAAAAAAAAAAAAAAAAAAAAA-3' (SEQ ID NO: 12), and the nucleotide sequence of the solid phase probe (DNA) is 5'-TTTTTTTTTTTTTTTTTTTTTT-3' (SEQ ID NO: 1, the 5'-end is biotin-labeled); those artificially synthesized by Hokkaido System Science Co., Ltd. were used. The capture probe was designed such that, when a hybrid of the target nucleic acid and the solid phase probe was formed, the modified nucleobase [C] would be present in the single-stranded structure part of the hybrid.

The measurement of the modified nucleobase using the capture probe and the solid phase probe was carried out by a method similar to that in Example 2 except that a different target nucleic acid was used in different amounts (10 pmol, 1 pmol, 0.1 pmol, or 0.01 pmol) and that a different capture probe and a different solid phase probe were used.

Figure 6:
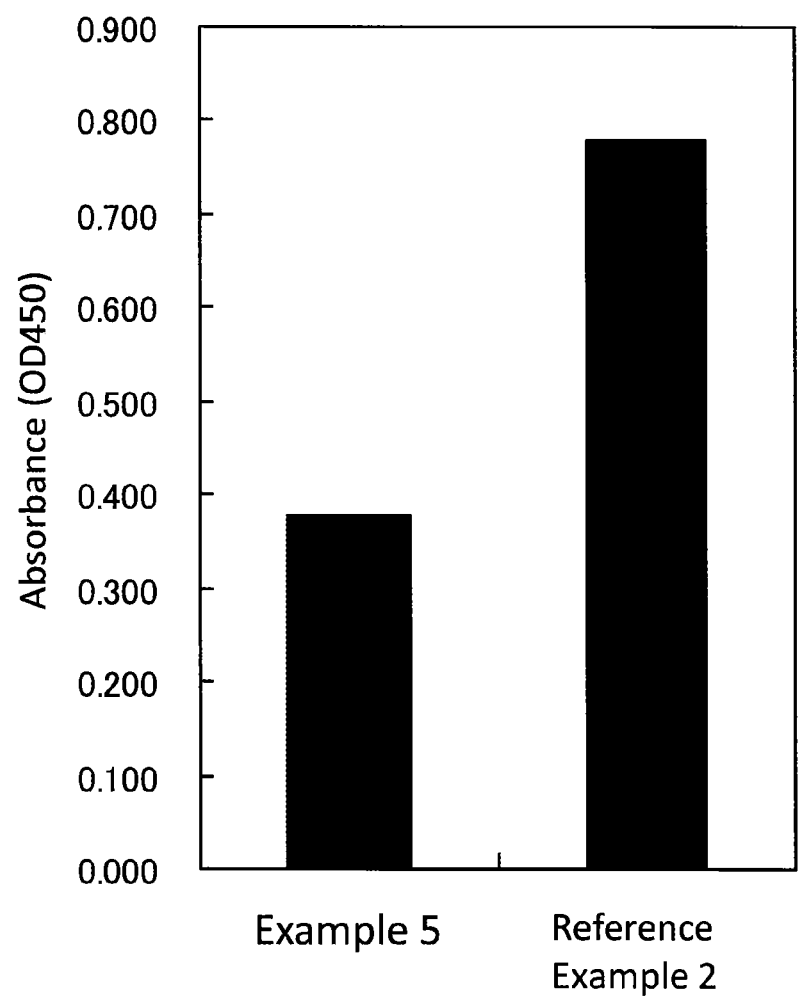
FIG. 6 is a diagram of signal values (background values) measured in measurement on the conditions of the target nucleic acid containing the modified nucleobase (0 mol), the capture probe (+), the solid phase probe (+: Example 5; −: Reference Example 2), and the antibody against the modified nucleobase (+).
Figure 7:
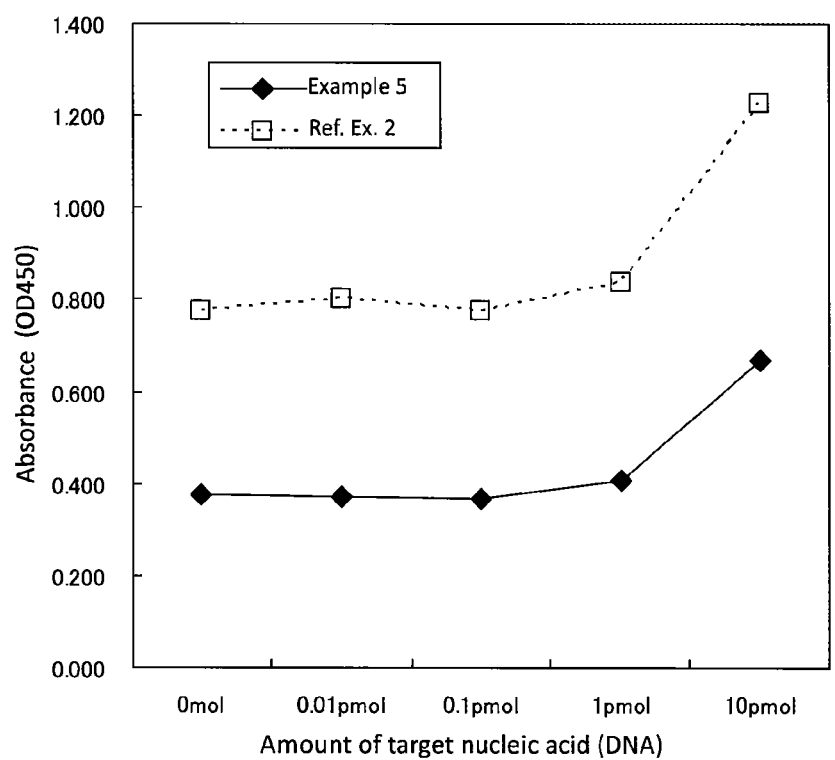
FIG. 7 is a diagram of signal values measured in measurement on the conditions of the target nucleic acid containing the modified nucleobase (0 mol, 0.01 pmol, 0.1 pmol, 1 mol, or 10 pmol), the capture probe (+), the solid phase probe (+: Example 5; −: Reference Example 2), and the antibody against the modified nucleobase (+).

As a result of the measurement, even when the capture probe was designed such that, when the hybrid of the target nucleic acid, the capture probe, and the solid phase probe was formed, the modified nucleobase [C] would be present in the single-stranded structure part of the hybrid, reductions in the background value and increases in the S/N value were revealed (Table 8 and FIGS. 6 and 7).

Reference Example 2

Use of Capture Probe in Measurement of Modified Nucleobase (2)

The nucleotide sequence of the target nucleic acid (DNA) is 5'-AATCAG[C]GGGAGCTCTTTCTTTGCGCG-GCGTCCGTCCTGTTGACTTC-3' (SEQ ID NO: 19, [C] is 5-methylcytosine), and the nucleotide sequence of the capture probe (DNA) for capturing the target nucleic acid is 5'-GAAGTCAACAGGACGACGCCGCGCAA-3' (SEQ ID NO: 18, the 5'-end is biotin-labeled); those artificially synthesized by Hokkaido System Science Co., Ltd. were used.

The measurement of the modified nucleobase using the capture probe was carried out as follows. First, the target nucleic acid containing 5-methylcytosine (10 pmol, 1 pmol, 0.1 pmol, or 0.01 pmol) and the capture probe (5 pmol) were dissolved in 100 µL of a hybridization buffer (4×SSC, 0.1% SDS) and were reacted at 60° C. for 2 hours to form a hybrid of the target nucleic acid and the capture probe. A solution not containing the target nucleic acid was also prepared, and a similar operation was performed. The solution after the hybridization reaction in an amount of 100 µL was added to a streptavidin-coated plate (manufactured by Thermo Scientific) and was reacted at 37° C. for 30 minutes to immobilize a nucleic acid hybrid on the streptavidin plate. The streptavidin plate was washed twice with 300 µL of PBS-T, and 500 ng/mL of the anti-methylcytosine antibody (Clone33D3 manufactured by Millipore Corporation) was added thereto by 50 µL each and was reacted at 37° C. for 1 hour. The streptavidin plate was washed three times with 300 µL of PBS-T, and 500 ng/mL of the peroxidase-labeled anti-IgG antibody (manufactured by Thermo Scientific) was added thereto by 50 µL each and was reacted at 37° C. for 30 minutes. After the streptavidin plate was washed three times with 300 µL of PBS-T, 3,3',5,5'-tetramethylbenzidine was added thereto by 100 µL each and was reacted in a dark place at room temperature for 7 minutes. Thereafter, a 2N hydrochloric acid solution was added thereto by 100 µL each, and absorbance at 450 nm was measured by the microplate reader (Arvo manufactured by PerkinElmer, Inc.).

The results were as listed and illustrated in Table 8 and FIGS. 6 and 7.

TABLE 8

| | Methodology | Target nucleic acid (DNA) | OD450 | S/N |
|---|---|---|---|---|
| Example 5 | Use of solid phase probe and capture probe in combination (two-step hybridization) | 10 pmol | 0.670 | 1.77 |
| | | 1 pmol | 0.406 | 1.07 |
| | | 0.1 pmol | 0.366 | 0.97 |
| | | 0.01 pmol | 0.373 | 0.99 |
| | | 0 mol | 0.378* | |
| Reference example 2 | Use of capture probe alone (one-step hybridization) | 10 pmol | 1.228 | 1.58 |
| | | 1 pmol | 0.839 | 1.08 |
| | | 0.1 pmol | 0.776 | 1.00 |
| | | 0.01 pmol | 0.800 | 1.03 |
| | | 0 mol | 0.778* | |

*Background value

Example 6

Use of Solid Phase Probe and Capture Probe in Measurement of Modified Nucleobase (5)

The nucleotide sequence of the target nucleic acid (DNA) is 5'-G[C]GGAGCTCTCCCT[C]GGGA[C]GGTGGCA-GCCTCGAGTGGTCCTGCA-3' SEQ ID NO: 20, [C] is 5-methylcytosine), the nucleotide sequence of the capture probe (DNA) for capturing the target nucleic acid is 5'-AAAAAAAAAAAAAAAAAAAAATGCAGGAC-CACTCGAGGCTGCCAC-3' (SEQ ID NO: 21), and the nucleotide sequence of the solid phase probe (DNA) is 5'-TTTTTTTTTTTTTTTTTTTT-3' (SEQ ID NO: 1, the 5'-end is biotin-labeled); those artificially synthesized by Hokkaido System Science Co., Ltd. were used. The capture probe was designed such that, when a hybrid of the target nucleic acid and the solid phase probe was formed, the modified nucleobase [C] would be present in the single-stranded structure part of the hybrid.

The measurement of the modified nucleobase using the capture probe and the solid phase probe was carried out as follows. First, 5 pmol of the solid phase probe was dissolved in 100 μL of a PBS buffer solution, and the whole amount thereof was added to a streptavidin-coated plate (manufactured by Thermo Scientific) and was reacted at 37° C. for 30 minutes to immobilize the solid phase probe on the streptavidin plate. The streptavidin plate was washed twice with 300 μL of PBS-T, and 100 μL of a solution containing the target nucleic acid containing 5-methylcytosine (1 pmol, 0.1 pmol, 0.01 pmol, or 0.001 pmol) and the capture probe (5 pmol) in a hybridization buffer (4×SSC, 0.3% Tween20) was added thereto, was reacted at 60° C. for 2 hours, and was then reacted at 37° C. for 30 minutes to form a hybrid of three parties, that is, the target nucleic acid, the capture probe, and the solid phase probe. For a solution not containing the target nucleic acid, a similar operation was performed. The streptavidin plate was washed twice with 300 μL of PBS-T, and 50 ng/mL of the anti-methylcytosine antibody (Clone33D3 manufactured by Nippon Gene Co., Ltd.) was added thereto by 100 μL each and was reacted at 37° C. for 1 hour. The streptavidin plate was washed three times with 300 μL of PBS-T, and 250 ng/mL of the peroxidase-labeled anti-IgG antibody (manufactured by Thermo Scientific) was added thereto by 100 μL each and was reacted at 37° C. for 30 minutes. After the streptavidin plate was washed three times with 300 μL of PBS-T, 3,3',5,5'-tetramethylbenzidine was added thereto by 100 μL each and was reacted in a dark place at room temperature for 15 minutes. Thereafter, a 2N hydrochloric acid solution was added thereto by 100 μL each, and absorbance at 450 nm was measured by the microplate reader (Arvo manufactured by PerkinElmer, Inc.).

Figure 8:
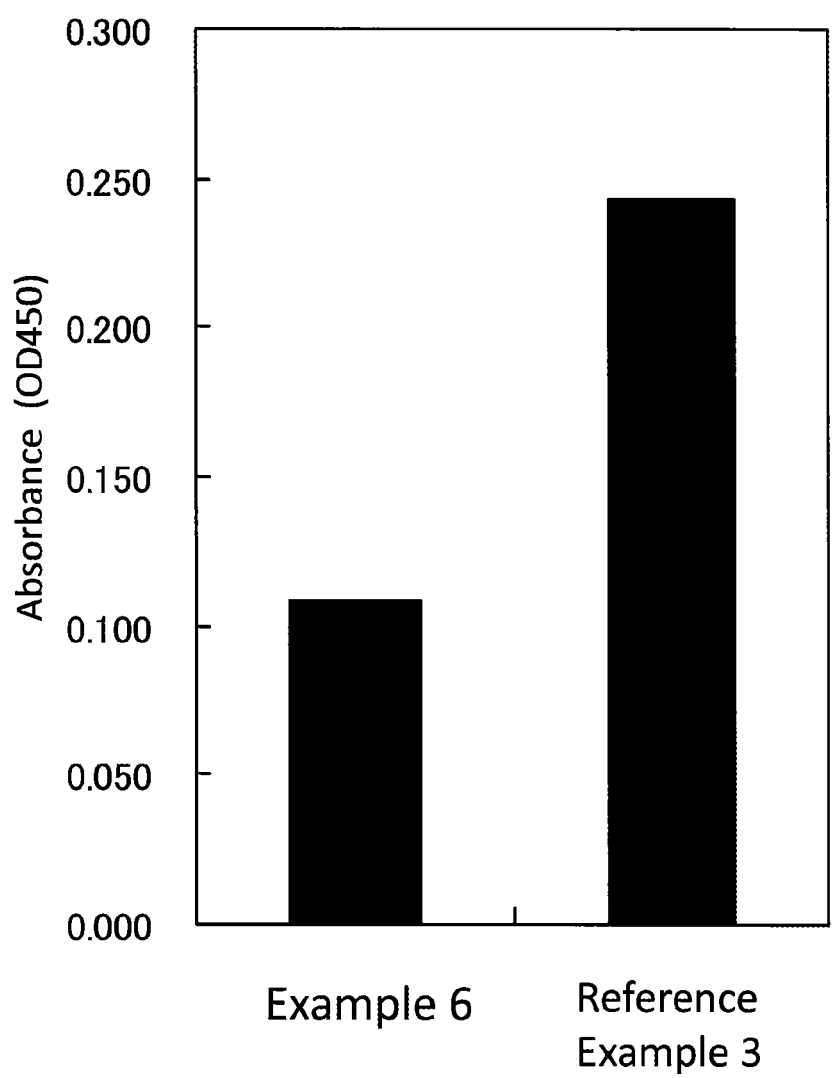
FIG. 8 is a diagram of signal values (background values) measured in measurement on the conditions of the target nucleic acid containing the modified nucleobase (0 mol), the capture probe (+), the solid phase probe (+: Example 6; −: Reference Example 3), and the antibody against the modified nucleobase (+).
Figure 9:
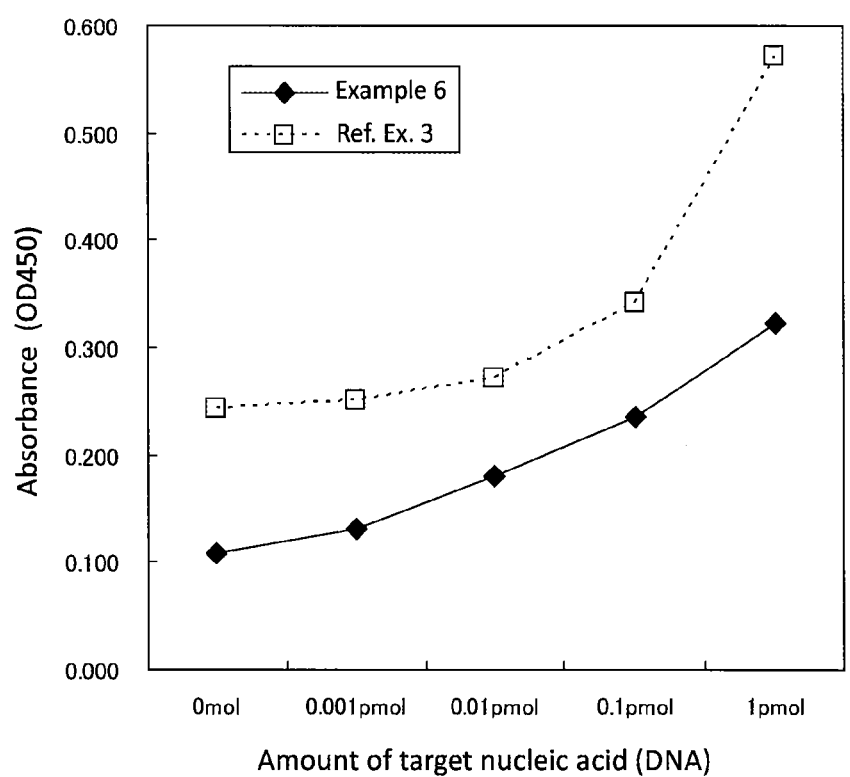
FIG. 9 is a diagram of signal values measured in measurement on the conditions of the target nucleic acid containing the modified nucleobase (0 mol, 0.01 pmol, 0.1 pmol, 1 mol, or 10 pmol), the capture probe (+), the solid phase probe (+: Example 6; −: Reference Example 3), and the antibody against the modified nucleobase (+).

As a result of the measurement, in the measurement of the modified nucleobase using the capture probe and the solid phase probe, even when the target nucleic acid and the capture probe different from those of Example 2 and Example 5 were used, reductions in the background value and increases in the S/N value were revealed (Table 9 and FIGS. 8 and 9). Interestingly, in the present test using the target nucleic acid containing a plurality of modified nucleobases, although use of the capture probe and the solid phase probe in combination showed a more linear relation (the slope is nearly constant) between a concentration range (0.001 pmol to 1 pmol) of the target nucleic acid and the detection signal value, use of the capture probe alone revealed almost no change in the detection signal value in a low concentration range (0 pmol to 0.01 pmol) of the target nucleic acid (FIG. 9). This fact suggests that use of the capture probe and the solid phase probe in combination amplifies detection sensitivity in the low concentration range (e.g., 0 pmol to 0.01 pmol) of the target nucleic acid containing the modified nucleobases.

Reference Example 3

Use of Capture Probe in Measurement of Modified Nucleobase (3)

The nucleotide sequence of the target nucleic acid (DNA) is 5'-G[C]GGAGCTCTCCCT[C]GGGA[C]GGTGGCA-GCCTCGAGTGGTCCTGCA-3' (SEQ ID NO: 20, [C] is 5-methylcytosine), and the nucleotide sequence of the capture probe (DNA) for capturing the target nucleic acid is 5'-TGCAGGACCACTCGAGGCTGCCAC-3' (SEQ ID NO: 22, the 5'-end is biotin-labeled); those artificially synthesized by Hokkaido System Science Co., Ltd. were used.

The measurement of the modified nucleobase using the capture probe was carried out as follows. First, the target nucleic acid containing 5-methylcytosine (1 pmol, 0.1 pmol, 0.01 pmol, or 0.001 pmol) and the capture probe (5 pmol) were dissolved in 100 μL of a hybridization buffer (4×SSC, 0.3% Tween20) and were reacted at 60° C. for 2 hours to form a hybrid of the target nucleic acid and the capture probe. A solution not containing the target nucleic acid was also prepared, and a similar operation was performed. The solution after the hybridization reaction in an amount of 100 μL was added to a streptavidin-coated plate (manufactured by Thermo Scientific) and was reacted at 37° C. for 30 minutes to immobilize a nucleic acid hybrid on the streptavidin plate. The streptavidin plate was washed twice with 300 μL of PBS-T, and 50 ng/mL of the anti-methylcytosine antibody (Clone33D3 manufactured by Nippon Gene Co., Ltd.) was added thereto by 100 μL each and was reacted at 37° C. for 1 hour. The streptavidin plate was washed three times with 300 μL of PBS-T, and 250 ng/mL of the peroxidase-labeled anti-IgG antibody (manufactured by Thermo Scientific) was added thereto by 100 μL each and was reacted at 37° C. for 30 minutes. After the streptavidin plate was washed three times with 300 μL of PBS-T, 3,3',5,5'-tetramethylbenzidine was added thereto by 100 μL each and was reacted in a dark place at room temperature for 15 minutes. Thereafter, a 2N hydrochloric acid solution was added thereto by 100 μL each, and absorbance at 450 nm was measured by the microplate reader (Arvo manufactured by PerkinElmer, Inc.).

The results were as listed and illustrated in Table 9 and FIGS. 8 and 9.

TABLE 9

| Methodology | | Target nucleic acid (DNA) | OD450 | S/N |
|---|---|---|---|---|
| Example 6 | Use of solid phase probe and capture probe in combination (two-step hybridization) | 1 pmol | 0.323 | 2.98 |
| | | 0.1 pmol | 0.236 | 2.18 |
| | | 0.01 pmol | 0.180 | 1.66 |
| | | 0.001 pmol | 0.131 | 1.21 |
| | | 0 mol | 0.108* | |
| Reference example 3 | Use of capture probe alone (one-step hybridization) | 1 pmol | 0.571 | 2.35 |
| | | 0.1 pmol | 0.341 | 1.40 |
| | | 0.01 pmol | 0.272 | 1.12 |
| | | 0.001 pmol | 0.251 | 1.03 |
| | | 0 mol | 0.243* | |

*Background value

Example 7

Use of Solid Phase Probe and Capture Probe in Measurement of Modified Nucleobase (6)

The nucleotide sequence of the target nucleic acid (DNA) is 5'-G[C]GCAC[C]GTTTG[C]GACTTGGTGAGT-GTCTGGGT[C]GCCT[C]GCTCC-3' (SEQ ID NO: 23, [0] is 5-methylcytosine), the nucleotide sequence of the capture probe (DNA) for capturing the target nucleic acid is 5'-AAAAAAAAAAAAAAAAAAAAAACCCAGACACT-CACCAAGTC-3' (SEQ ID NO: 24), and the nucleotide sequence of the solid phase probe (DNA) is 5'-TTTTTTTTTTTTTTTTTTTT-3' (SEQ ID NO: 1, the 5'-end is biotin-labeled); those artificially synthesized by Hokkaido System Science Co., Ltd. were used. The capture probe was designed such that, when a hybrid of the target nucleic acid and the solid phase probe was formed, the modified nucleobase [C] would be present in the single-stranded structure part of the hybrid.

The measurement of the modified nucleobase using the capture probe and the solid phase probe was carried out by a method similar to that in Example 6 except that a different target nucleic acid and a different capture probe were used.

Figure 10:
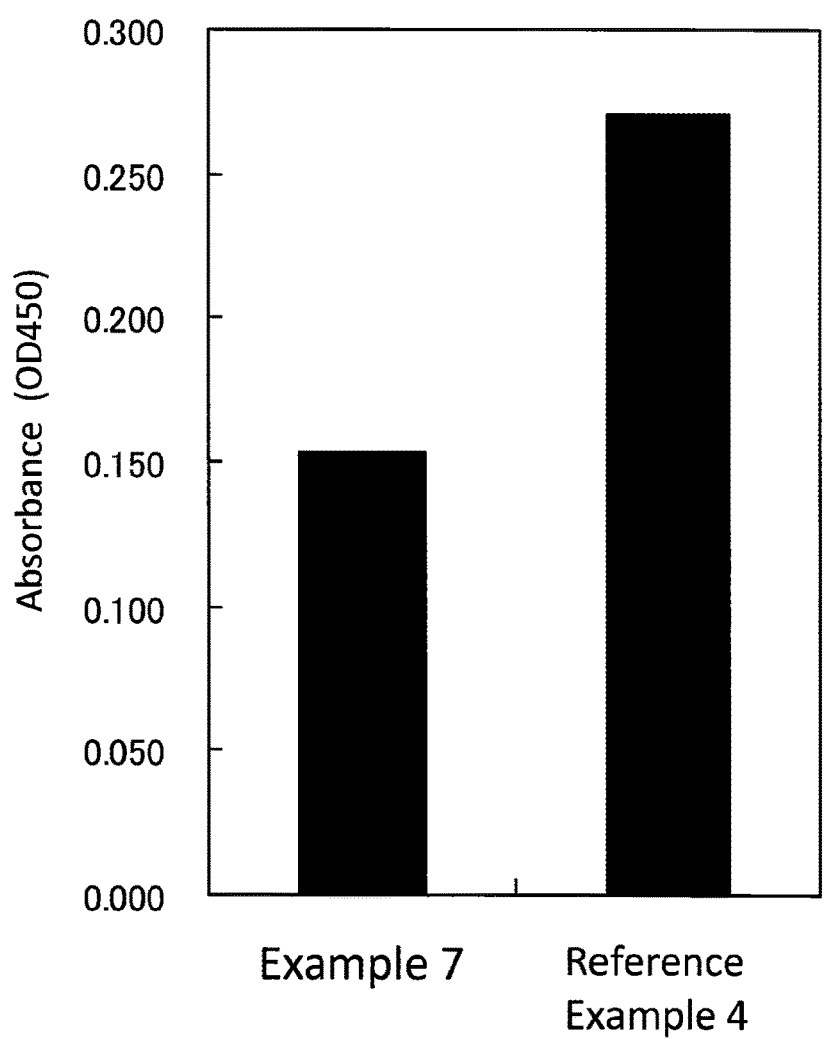
FIG. 10 is a diagram of signal values (background values) measured in measurement on the conditions of the target nucleic acid containing the modified nucleobase (0 mol), the capture probe (+), the solid phase probe (+: Example 7; −: Reference Example 4), and the antibody against the modified nucleobase (+).
Figure 11:
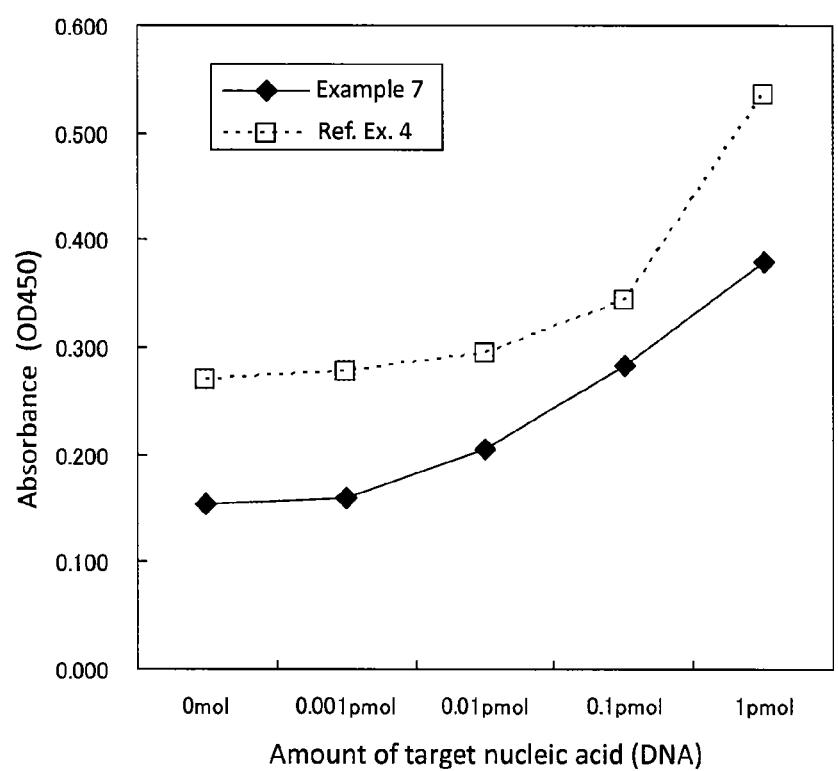
FIG. 11 is a diagram of signal values measured in measurement on the conditions of the target nucleic acid containing the modified nucleobase (0 mol, 0.01 pmol, 0.1 pmol, 1 mol, or 10 pmol), the capture probe (+), the solid phase probe (+: Example 7; −: Reference Example 4), and the antibody against the modified nucleobase (+).

As a result of the measurement, in the measurement of the modified nucleobase using the capture probe and the solid phase probe, even when the target nucleic acid and the capture probe different from those of Example 2, Example 5, and Example 6 were used, reductions in the background value and increases in the S/N value were revealed (Table 10 and FIGS. 10 and 11). Interestingly, in the present test using the target nucleic acid containing a plurality of modified nucleobases, although use of the capture probe and the solid phase probe in combination showed a more linear relation (the slope is nearly constant) between a concentration range (0.001 pmol to 1 pmol) of the target nucleic acid and the detection signal value, use of the capture signal alone revealed almost no change in the signal value in a low concentration range (0 pmol to 0.01 pmol) of the target nucleic acid (FIG. 11). This fact suggests that use of the capture probe and the solid phase probe in combination amplifies detection sensitivity in the low concentration range (e.g., 0 pmol to 0.01 pmol) of the target nucleic acid containing the modified nucleobases.

Reference Example 4

Use of Capture Probe in Measurement of Modified Nucleobase (4)

The nucleotide sequence of the target nucleic acid (DNA) is 5'-G[C]GCAC[C]GTTTG[C]GACTTGGTGAGT-GTCTGGGT[C]GCCT[C]GCTCC-3' (SEQ ID NO: 23, [C] is 5-methylcytosine), and the nucleotide sequence of the capture probe (DNA) for capturing the target nucleic acid is 5'-ACCCAGACACTCACCAAGTC-3' (SEQ ID NO: 25, the 5'-end is biotin-labeled); those artificially synthesized by Hokkaido System Science Co., Ltd. were used.

The measurement of the modified nucleobase using the capture probe was carried out by a method similar to that in Reference Example 3 except that a different target nucleic acid and a different capture probe were used.

The results were as listed and illustrated in Table 10 and FIGS. 10 and 11.

TABLE 10

| Methodology | | Target nucleic acid (DNA) | OD450 | S/N |
|---|---|---|---|---|
| Example 7 | Use of solid phase probe and capture probe in combination (two-step hybridization) | 1 pmol | 0.380 | 2.49 |
| | | 0.1 pmol | 0.284 | 1.86 |
| | | 0.01 pmol | 0.206 | 1.35 |
| | | 0.001 pmol | 0.159 | 1.04 |
| | | 0 mol | 0.153* | |
| Reference example 4 | Use of capture probe alone (one-step hybridization) | 1 pmol | 0.535 | 1.98 |
| | | 0.1 pmol | 0.343 | 1.27 |
| | | 0.01 pmol | 0.294 | 1.09 |
| | | 0.001 pmol | 0.277 | 1.03 |
| | | 0 mol | 0.270* | |

*Background value

Example 8

Use of Heterogeneous Nucleic Acid Probe in Measurement System of Present Invention The nucleotide sequence of the target nucleic acid (DNA) is 5'-TTGCGCGGCGTC[C]GTCCTGTTGACTTC-3' (SEQ ID NO: 11, [C] is 5-methylcytosine), the nucleotide sequence of the capture probe (heterogeneous nucleic acid probe: 2'-O-methylated RNA+DNA) for capturing the target nucleic acid is 5'-GAAGUCAACAGGACGACGCCGCG-CAAAAAAAAAAAAAAAAAAAAAA-3' (SEQ ID NO: 26, the backbone of the 1st to 26th nucleotide residues on the 5'-end side is 2'-O-methylated RNA, whereas the backbone of the 27th to 48th nucleotide residues is DNA), and the nucleotide sequence of the solid phase probe is 5'-TTTTTTTTTTTTTTTTTTTT-3' (SEQ ID NO: 1, the 5'-end is biotin-labeled); those artificially synthesized by Hokkaido System Science Co., Ltd. were used. The capture probe was designed such that, when a hybrid of the target nucleic acid and the solid phase probe was formed, an unpaired part would be formed at the modified nucleobase [C] in the double-stranded structure part composed of the target nucleic acid and the capture probe.

The measurement (Experiment 1) of the modified nucleobase using the heterogeneous nucleic acid probe was carried out by a method similar to that in Example 6 except that a different target nucleic acid and a different capture probe were used.

Next, the measurement (Experiment 2) of the modified nucleobase was carried out similarly using a homogeneous nucleic acid probe. Experiment 2 was carried out by a method similar to that in Experiment 1 except that the homogeneous nucleic acid probe (to the target nucleic acid) (5'-GAAGTCAACAGGACGACGCCGCG-CAAAAAAAAAAAAAAAAAAAAAAA-3' (SEQ ID NO: 12)) with DNA as the backbone was used in place of the capture probe with 2'-O-methylated RNA as the partial backbone used in Experiment 1. Experiment 2 is similar to Example 2 in terms of the type of the used target nucleic acid (DNA), capture probe (DNA), and solid phase probe (DNA).

Absorbance (heterogeneous) measured in Experiment 1 was divided by absorbance (homogeneous) measured in Experiment 2 to determine an OD450 ratio (heterogeneous/homogeneous). The ratio (heterogeneous/homogeneous) of the background value corresponds to a value determined by dividing absorbance (a background value (heterogeneous)) measured in the absence (that is, 0 pmol) of the target nucleic acid containing the modified nucleobase in Experiment 1 by absorbance (a background value (homogeneous)) measured in the absence (that is, 0 pmol) of the target nucleic acid containing the modified nucleobase in Experiment 2.

S/N (heterogeneous) and S/N (homogeneous) were calculated from the absorbance measured in Experiment 1 and Experiment 2, and subsequently S/N (heterogeneous) was divided by S/N (homogeneous) to determine S/N (heterogeneous/homogeneous). Concerning S/N (heterogeneous) and S/N (homogeneous), S indicates absorbance measured in the presence of the target nucleic acid containing the modified nucleobase (1 ppmol, 1 pmol, 0.1 pmol, or 0.01 pmol), whereas N indicates absorbance (a background value) measured in the absence (that is, 0 pmol) of the target nucleic acid containing the modified nucleobase. The results are listed in Table 11.

As a result of the measurement, as is clear from the ratio (heterogeneous/homogeneous) of the background value, the heterogeneous nucleic acid probe suppressed the background value compared with the homogeneous nucleic acid probe (Table 11). When the amount of the target nucleic acid was smaller (0.1 pmol or less, or especially 0.01 pmol or less, for example) or, in other words, when the concentration of the target nucleic acid in the solution was lower (1 nM or less, or especially 0.1 nM or less, for example), reductions in the OD450 ratio (heterogeneous/homogeneous) were revealed (Table 11). Furthermore, when the amount of the target nucleic acid was larger (0.1 pmol or more, or especially 1 pmol or more, for example) or, in other words, when the concentration of the target nucleic acid in the solution was high (1 nM or more, or especially 10 nM or more, for example), increases in the S/N ratio (heterogeneous/homogeneous) were revealed (Table 11).

TABLE 11

| Target nucleic acid (DNA) | OD450 ratio (heterogeneous/homogeneous) | S/N ratio (heterogeneous/homogeneous) |
|---|---|---|
| 1 pmol | 0.732 | 1.80 |
| 0.1 pmol | 0.517 | 1.26 |
| 0.01 pmol | 0.413 | 1.02 |
| 0.001 pmol | 0.419 | 0.99 |
| 0 pmol | 0.410* | |

*Background value ratio (heterogeneous/homogeneous)

The above results will be described as follows:

1) When the target nucleic acid was absent, or when the concentration of the target nucleic acid was low, the heterogeneous nucleic acid probe further suppressed the detection signal value compared with the homogeneous nucleic acid probe. Within the range of the used amount of the target nucleic acid, concerning suppression of the detection signal value, the heterogeneous nucleic acid probe produced a finer effect than the homogeneous nucleic acid probe on all occasions.

2) When the used amount of the target nucleic acid was small, the S/N value measured using the heterogeneous nucleic acid probe was comparable to the S/N value measured using the homogeneous nucleic acid probe. In contrast, when the used amount of the target nucleic acid was large, the heterogeneous nucleic acid probe further increased the S/N value compared with the homogeneous nucleic acid probe. In other words, concerning the S/N value, the heterogeneous nucleic acid probe produced an effect comparable to the homogeneous nucleic acid probe or more on all occasions.

From the foregoing, it has been revealed that use of the heterogeneous nucleic acid probe in the method of the present invention is useful.

INDUSTRIAL APPLICABILITY

The method and kit of the present invention is useful for measuring a modified nucleobase.

The invention claimed is:

1. A method for measuring a modified nucleobase, the method comprising:
   (1) incubating a nucleic acid sample, a capture probe, and a solid phase probe in a solution; and
   (2) measuring the modified nucleobase using an antibody against the modified nucleobase in the solution obtained at (1),
   wherein the nucleic acid sample comprises a target nucleic acid containing the modified nucleobase, and the steps (1) and (2) are performed by (1') and (2'), respectively:
   (1') reacting the nucleic acid sample containing the target nucleic acid containing the modified nucleobase, the capture probe, and the solid phase probe in the solution by incubation to form a hybrid composed of the target nucleic acid, the capture probe, and the solid phase probe; and
   (2') measuring the modified nucleobase using the antibody against the modified nucleobase in the solution containing the hybrid,
   wherein the capture probe is a nucleic acid molecule that can hybridize with the target nucleic acid and the solid phase probe,
   wherein the solid phase probe is poly A or poly T,
   wherein the modified nucleobase is methylcytosine,
   wherein the capture probe is a probe containing a nucleic acid heterogeneous to the target nucleic acid.

2. The method according to claim 1, wherein the target nucleic acid is a target nucleic acid potentially containing two or more modified nucleobases.

3. The method according to claim 1, further comprising adding a solution containing the nucleic acid sample and the capture probe to a solid phase immobilized with the solid phase probe to prepare the solution containing the nucleic acid sample, the capture probe, and the solid phase probe.

4. The method according to claim 1, wherein a nucleobase that composes the modified nucleobase is cytosine.

5. The method according to claim 1, wherein the capture probe is designed such that an unpaired part of the modified nucleobase is formed in a double-stranded structure part composed of the target nucleic acid and the capture probe in the hybrid.

6. The method according to claim 1, wherein the capture probe is designed such that the modified nucleobase is present in a single-stranded structure part of the hybrid.

7. The method according to claim 1, wherein the measurement of the modified nucleobase using the antibody against the modified nucleobase is performed by ELISA.

8. A kit for measuring a modified nucleobase, the kit comprising:
   (I) a capture probe;
   (II) a solid phase probe; and
   (III) an antibody against the modified nucleobase,
   wherein the capture probe is a nucleic acid molecule that can hybridize with a target nucleic acid containing the modified nucleobase and the solid phase probe,
   wherein the solid phase probe is poly A or poly T,
   wherein the modified nucleobase is methylcytosine,
   wherein the target nucleic acid is contained in a nucleic acid sample,
   wherein the capture probe is a probe containing a nucleic acid heterogeneous to the target nucleic acid.

* * * * *